United States Patent [19]

Kasina et al.

[11] Patent Number: 5,175,257

[45] Date of Patent: * Dec. 29, 1992

[54] RADIOLABELED PROTEINS FOR DIAGNOSTIC OR THERAPEUTIC USE

[75] Inventors: Sudhakar Kasina; Ananthachari Srinivasan, both of Kirkland; John M. Reno, Brier; Linda M. Gustavson; Jeffrey N. Fitzner, both of Seattle, all of Wash.; David S. Jones, San Diego, Calif.

[73] Assignee: NeoRx Corporation, Seattle, Wash.

[*] Notice: The portion of the term of this patent subsequent to May 12, 2009 has been disclaimed.

[21] Appl. No.: 641,158

[22] Filed: Jan. 14, 1991

Related U.S. Application Data

[63] Continuation-in-part of Ser. No. 457,480, Dec. 29, 1989, Pat. No. 5,112,953.

[51] Int. Cl.$^5$ ............... C07K 15/28; C07K 17/06; A61K 49/02
[52] U.S. Cl. ............... 530/391.5; 530/331; 530/391.3; 530/395; 530/351; 530/408; 530/409; 424/1.1; 534/10; 536/4.1; 549/419; 549/496; 548/548; 548/517; 260/998.2; 558/17; 558/254; 560/110; 560/251
[58] Field of Search ........... 530/331, 388, 390, 391.3, 530/391.5, 395, 351, 408, 409; 424/1.1; 534/10; 260/998.2; 536/4.1; 549/496, 419; 548/548, 517; 558/17, 254; 560/110, 251

[56] References Cited

U.S. PATENT DOCUMENTS

| | | | |
|---|---|---|---|
| 4,575,556 | 3/1986 | Byrne et al. | 549/63 |
| 4,625,014 | 11/1986 | Senter et al. | 530/300 |
| 4,673,562 | 6/1987 | Davison et al. | 424/1.1 |
| 4,861,869 | 8/1989 | Nicolotti et al. | 530/402 |
| 4,897,255 | 1/1990 | Fritzberg et al. | 424/1.1 |
| 4,963,682 | 10/1990 | Bodor | 546/338 |
| 4,963,688 | 10/1990 | Bodor | 546/316 |
| 4,965,392 | 10/1990 | Fritzberg et al. | 558/254 |
| 4,980,147 | 12/1990 | Fritzberg et al. | 424/1.1 |
| 4,986,979 | 1/1991 | Morgan, Jr. et al. | 424/1.1 |
| 5,000,960 | 3/1991 | Wallach | 424/450 |
| 5,037,631 | 8/1991 | Nosco | 424/1.1 |
| 5,112,953 | 5/1992 | Gustavson et al. | 530/391.5 |

FOREIGN PATENT DOCUMENTS 0173424 3/1986 European Pat. Off.
250013 12/1987 European Pat. Off.
284071 9/1988 European Pat. Off.

OTHER PUBLICATIONS

Blair et al., "Linkage of Cytotoxic Agents to Immunoglobulins," *J. Immun. Meth.* 59:129-143, 1983.

Dean et al., "Ester-Link Tc-99m Labeled Antibody-Bifunctional Chelator Conjugates Having Enhanced Whole-Body Clearance", *J. Nucl. Med.* 30:934, 1989 Abst. No. 874.

Franz et al., "Labelling of Antibodies with $^{64}$Cu Using a Conjugate Containing a Macrocyclic Amine Chelating Agent," *Nucl. Med. Biol.* 14:479-484, 1987.

Hadley et al., "Synthesis Radioiodination, and Evaluation of a Para-iodo-Benzyl Alcohol Ester Antibody Conjugate," *J. Nucl. Med.* 30:924-925, 1989 Abstract No. 830.

Haseman et al., "Metabolizable $^{111}$In Chelate conjugated anti-iodotype monoclonal antibody for radioimmunodetection of lymphoma in mice," *J. Nucl. Med.* 12:455-460, 1986.

March, *Advanced Organic Chemistry*, Second edition, 1977, pp. 20-22, McGraw-Hill Book Company, New York.

Meares et al., "Chelate Radiochemistry: cleavable linkers lead to altered levels of radioactivity in the liver," *Int. J. Cancer* 1988 (suppl. 2), pp. 99-102.

Paik et al., "Reduction of Background Activities by Introduction of a Diester Linkage Between Antibody and a Chelate in Radioimmunodetection of Tumor," *J. Nucl. Med.* 30:1693-1701, 1989.

Quadri et al., "Biodistribution of an In-111 Labeled Antibody DTPA Conjugate Containing Ester Bonds," *J. Nucl. med.* 27:959, 1986.

Verbruggen et al. (1987), "Evaluation of the Renal Excretion Characteristics of Tc-99m Mercaptoacetylglycine," *J. Nucl. Med.* 28:731, 1987 Abstract No. 737.

Verbruggen et al. (1988), "Evaluation of the Diastereomers of Tc-99m-Mercaptoacetylglycyl-D-Alanylglycine (Tc-99m-D-MAGAG) in Primates," *J. Nucl. Med.* 29:909-910, 1988 Abstract No. 705.

*Primary Examiner*—Christine M. Nucker
*Assistant Examiner*—Kay K. Kim
*Attorney, Agent, or Firm*—Seed and Berry

[57] ABSTRACT

Chelating compounds of specified $N_2S_2$ $N_3S$ derived structure are useful for radiolabeling targeting molecules such as antibodies. Cleavable ester orthioester linkers connect the radionuclide metal chelates to the antibodies. The radiolabeled antibodies have improved biodistribution properties, including reduced localization within the intestines and kidneys.

36 Claims, 15 Drawing Sheets

1. SYNTHESIS OF SERINESUCCINATE REAGENT 6

SYNTHESIS OF CYSTEINE-SERINE SUCCINATE LIGAND 13.

SYNTHESIS OF N₃S SERINE-SUCCINATE LIGAND 20.

ALTERNATIVE ROUTE TO 9 FOR THE SYNTHESIS OF LIGAND 13

RADIOLABELED PROTEINS FOR DIAGNOSTIC OR THERAPEUTIC USE

CROSS REFERENCE TO RELATED APPLICATIONS

This application is a continuation-in-part of U.S. patent application Ser. No. 07/457,480, filed Dec. 29, 1989 now U.S. Pat. No. 5,112,953.

BACKGROUND

Radiolabeled antibodies are used in a variety of diagnostic and therapeutic medical procedures. The increased specificity of monoclonal antibodies, compared to polyclonal antibodies, makes them even more useful for delivering diagnostic or therapeutic agents such as radioisotopes to desired target sites in vivo. A monoclonal antibody specific for a desired type of target cells such as tumor cells may be used to deliver a therapeutic radionuclide attached to the antibody to the target cells, thereby causing the eradcation of the undesired target cells. Alternatively a monoclonal antibody having a diagnostically effective radionuclide attached thereto may be administered, whereupon the radiolabeled antibody localizes on the target tissue. Conventional diagnostic procedures then may be used to detect the presence of the target sites within the patient.

One method for radiolabeling proteins such as antibodies involves attachment of radionuclide metal chelates to the proteins. Chelates having a variety of chemical structures have been developed for this purpose. The usefulness of such chelates is dependent upon a number of factors such as the stability of radionuclide binding within the chelate and the reactivity of the chelate with the desired protein. The efficiency of radiolabeling of the chelating compound to produce the desired radionuclide metal chelate also is important. Another consideration is the biodistribution of the radiolabeled antibody and catabolites thereof in vivo. Localization in non-target tissues limits the total dosage of a therapeutic radiolabeled antibody that can be administered, thereby decreasing the therapeutic effect. In diagnostic procedures, localization in non-target tissues may cause undesirable background and/or result in misdiagnosis. The need remains for improvement in these and other characteristics of radionuclide metal chelate compounds used for radiolabeling of proteins such as antibodies.

SUMMARY OF THE INVENTION

The present invention provides chelating compounds, the corresponding radionuclide metal chelates, and targeting molecules such as proteins radiolabeled therewith. The radiolabeled proteins of the present invention have use in various assays as well as in vivo diagnostic and therapeutic procedures. The protein may be a monoclonal antibody that binds to cancer cells, for example.

Compounds of the present invention include compounds of the formulas:

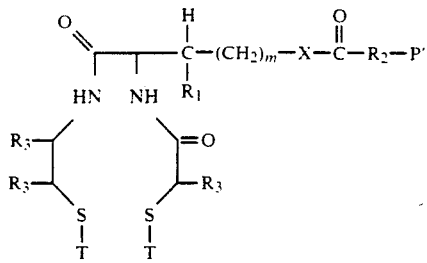

wherein:
m is 0 or 1;
$R_1$ represents H or $CH_3$;
X represents O or S;
each $R_3$ is independently selected from H, $CH_2OH$, $CH_3$, $-(CH_2)_n-CONH_2$, and $-(CH_2)_n-COOH$, wherein n is 0 to about 2, with at least one $R_3$ substituent being $-(CH_2)_n-COOH$;
T' and T each represent hydrogen or a sulfur protecting group;
$R_2$ represents a spacer; and
P' represents a targeting molecule or a conjugation group;

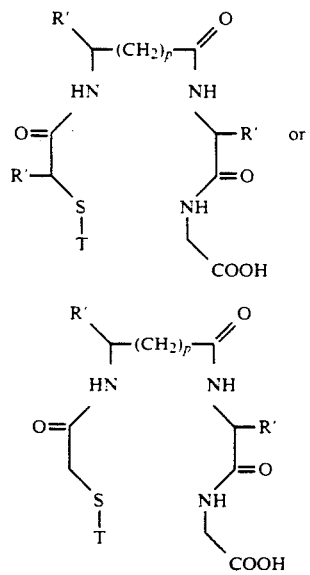

wherein
p is 0 or 1;
one of the R' symbols represents

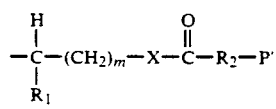

and the other(s) is/are selected from H, $CH_3$, $CH_2OH$, $-(CH_2)_n-CONH_2$ and $(CH_2)_n-COOH$ wherein n is 0 to about 2;
m is 0 or 1;
$R_1$ represents H or $CH_3$;
X represents O or S;
T represents hydrogen or a sulfur protecting group;
$R_2$ represents a spacer; and
P' represents a targeting molecule or a conjugation group;

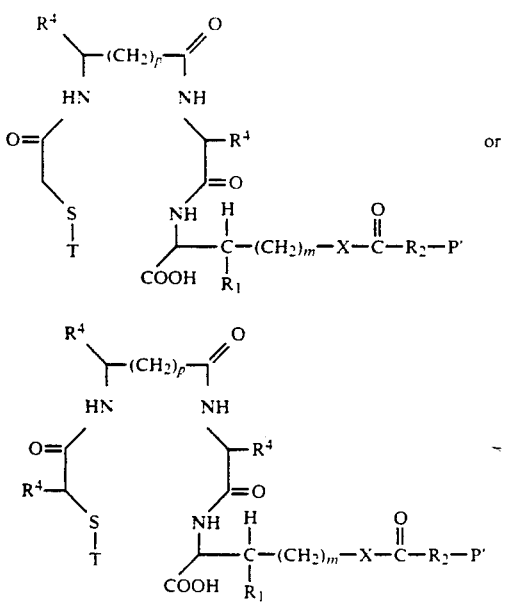

wherein
p is 0 or 1;
each $R_4$ is independently selected from H, $CH_3$, $CH_2OH$, $(CH_2)_n-CONH_2$ and $(CH_2)_n-COOH$ wherein n is 0 to about 2;
m is 0 or 1;
$R_1$ represents H or $CH_3$;
X represents O or S;
T represents hydrogen or a sulfur protecting group;
$R_2$ represents a spacer; and
P' represents a targeting molecule or a conjugation group; and

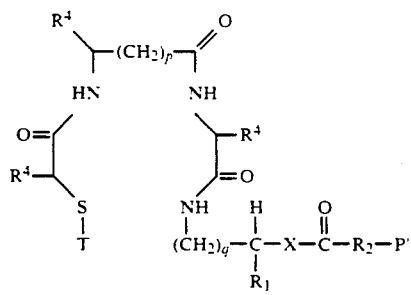

wherein
p is 0 or 1;
each $R_4$ is independently selected from H, $CH_3$, $CH_2OH$, $(CH_2)_n-CONH_2$ and $(CH_2)_n-COOH$ wherein n is 0 to about 2;
q is 1, 2, or 3;
$R_1$ represents H or $CH_3$;
X represents O or S;
T represents hydrogen or a sulfur protecting group;
$R_2$ represents a spacer; and
P' represents a targeting molecule or a conjugation group.

Reduction of undesirable localization of radioactivity within the kidneys and/or intestines has been achieved using the radiolabeled targeting molecules of the present invention. While not wishing to be bound by theory, the improved biodistribution properties are believed to be at least in part attributable to the presence and orientation of a cleavable ester within the linkage joining the chelate to the targeting molecule. The chemical structure of the chelating compounds and the resultant stereochemistry of the chelates released by cleavage of the linker also may play a role in reducing localization of radioactivity in the kidneys and intestines.

BRIEF DESCRIPTION OF THE DRAWINGS

FIG. 1 depicts a flow chart illustrating a procedure for the synthesis of serine succinate reagent.

FIG. 2 depicts a flow chart illustrating a procedure for the synthesis of cysteine-serine succinate ligand.

FIG. 3 depicts a flow chart illustrating a procedure for the synthesis of $N_3S$ serine succinate ligand.

FIG. 4 depicts a flow chart illustrating a procedure for the synthesis of N-(S-isobutyrylmercaptoacetyl)-O-(3-carbo-N'-hydroxysuccinimidylpropanoyl)-se ryl-glycylglycine.

FIG. 5 depicts a flow chart illustrating a procedure for the synthesis of $N_3S$ serine succinate ligand.

FIG. 6 depicts a flow chart illustrating a procedure for the preparation of radiolabeled protein.

FIGS. 7-9 depict a flow chart illustrating a procedure for the synthesis of $N_3S$ serine succinate ligand.

FIG. 10 depicts a flow chart illustrating a procedure for the synthesis of a precursor to the cysteine-serine succinate ligand of FIG. 2.

FIG. 16 depicts a flow chart illustrating a procedure for the synthesis of $N_3S$ serine succinate ligand.

In the figures, "ID" represents injected dose, "BL" represents blood, "LV" or "LI" represents liver, "ST" represents stomach, "KI" represents kidneys, and "IN" represents intestines.

Figure 11A:
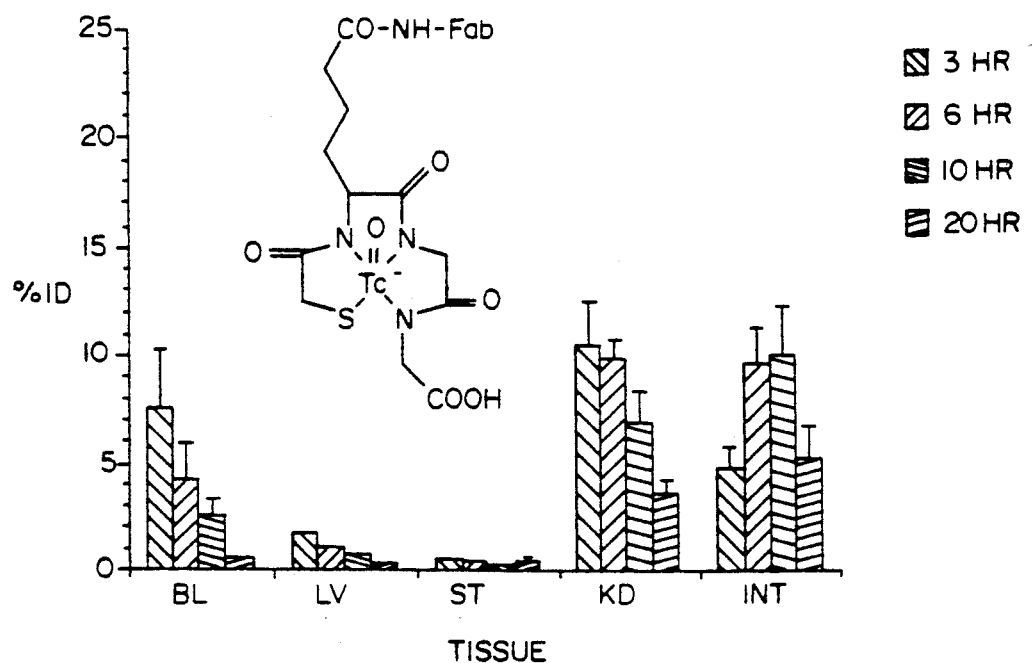
FIGS. 11-15 depict biodistribution data for antibodies radiolabeled with various radionuclide metal chelates.
Figure 11B:
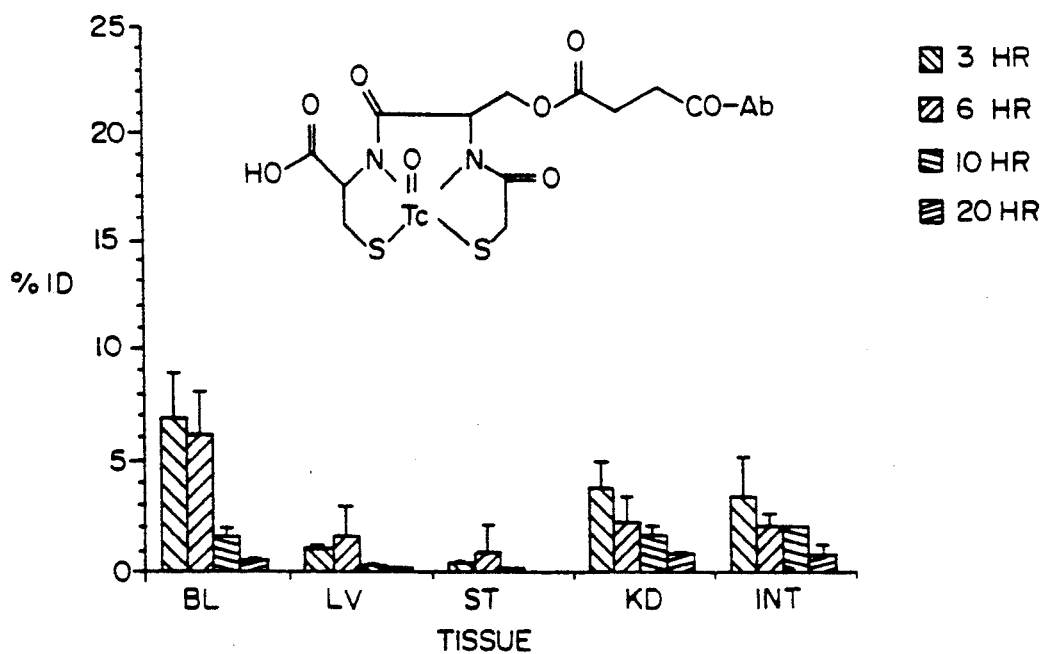

FIG. 11 graphically illustrates biodistribution of $^{99m}$Tc-labeled antibody fragments analyzed in a rat model. The top graph represents biodistribution data for an antibody fragment labeled with a $^{99m}$Tc-$N_3$S chelate wherein there is no ester linkage between the chelate and the antibody. The bottom graph represents biodistribution data for the same antibody fragment labeled with a $^{99m}$Tc-chelate prepared from compound 13 of FIG. 2.

Figure 12A:
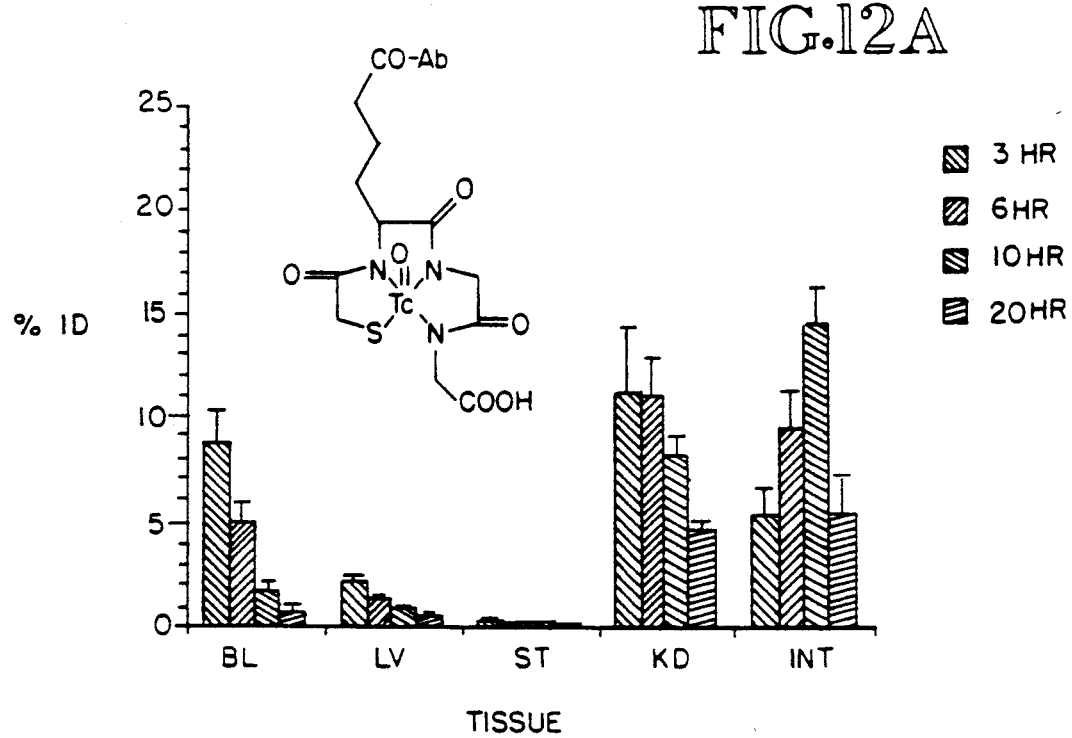
Figure 12B:
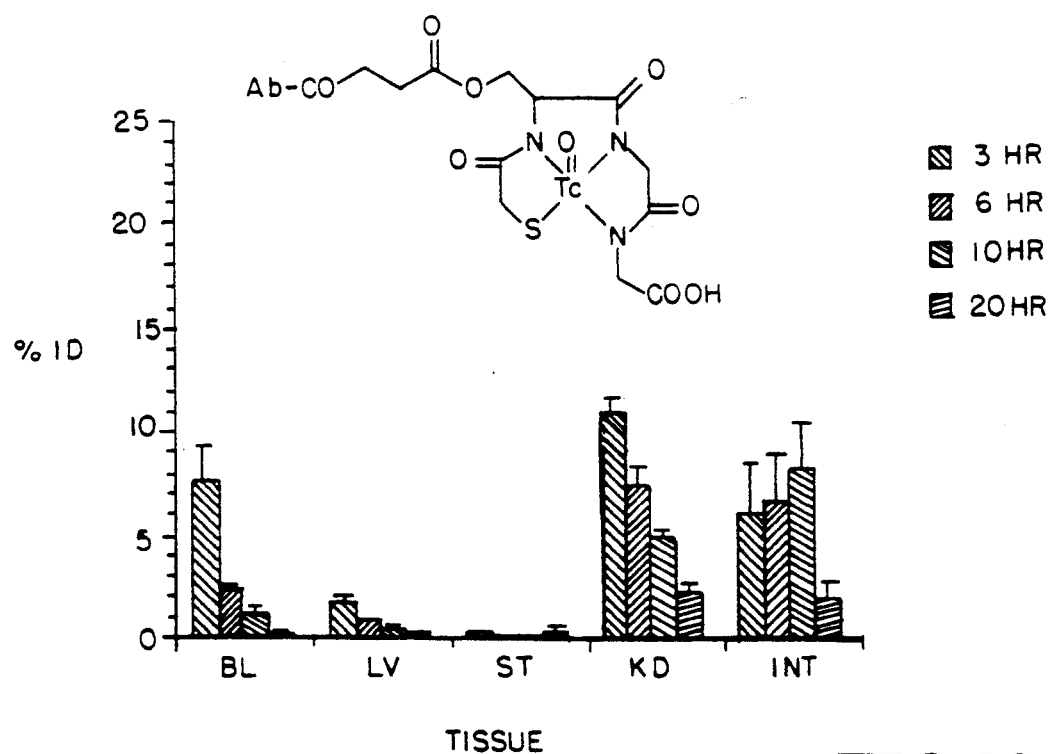

FIG. 12 graphically illustrates biodistribution of $^{99m}$Tc-labeled antibody fragments analyzed in a rat model. The top graph represents biodistribution data for an antibody fragment labeled with a $^{99m}$Tc-$N_3$S chelate wherein there is no ester linkage between the chelate and the antibody. The bottom graph represents biodistribution data for the same antibody fragment labeled with a $^{99m}$Tc-chelate prepared from compound 20 of FIG. 3.

Figure 13A:
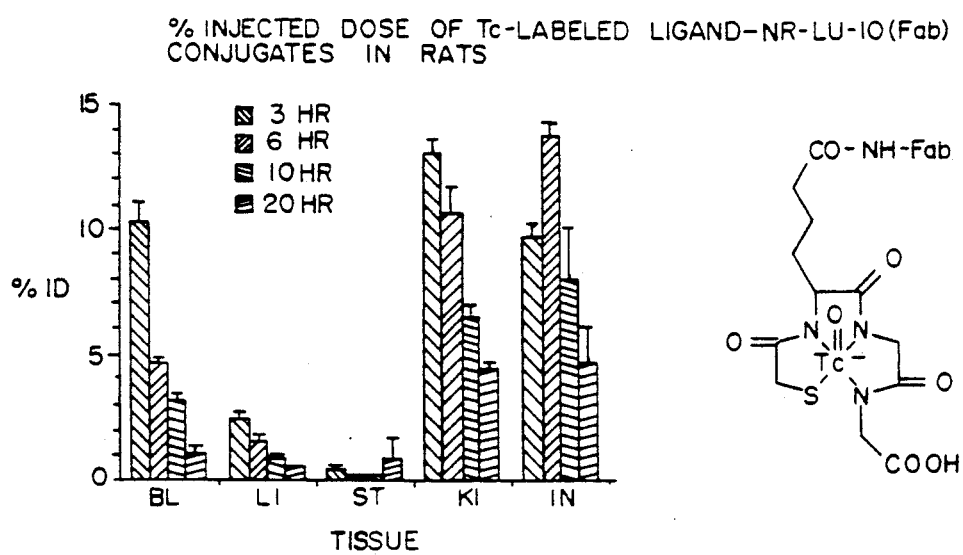
Figure 13B:
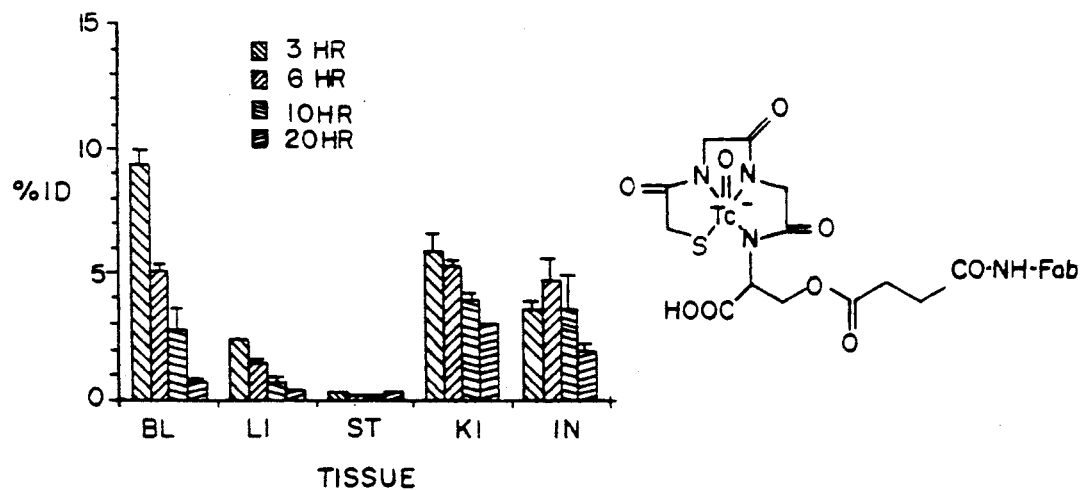

FIG. 13 graphically illustrates biodistribution of $^{99m}$Tc-labeled antibody fragments analyzed in a rat model. The top graph represents biodistribution data for an antibody fragment labeled with a $^{99m}$Tc-$N_3$S chelate wherein there is no ester linkage between the chelate and the antibody. The bottom graph represents biodistribution data for the same antibody fragment labeled with a $^{99m}$Tc-chelate prepared from compound 47 of FIG. 9.

Figure 14A:
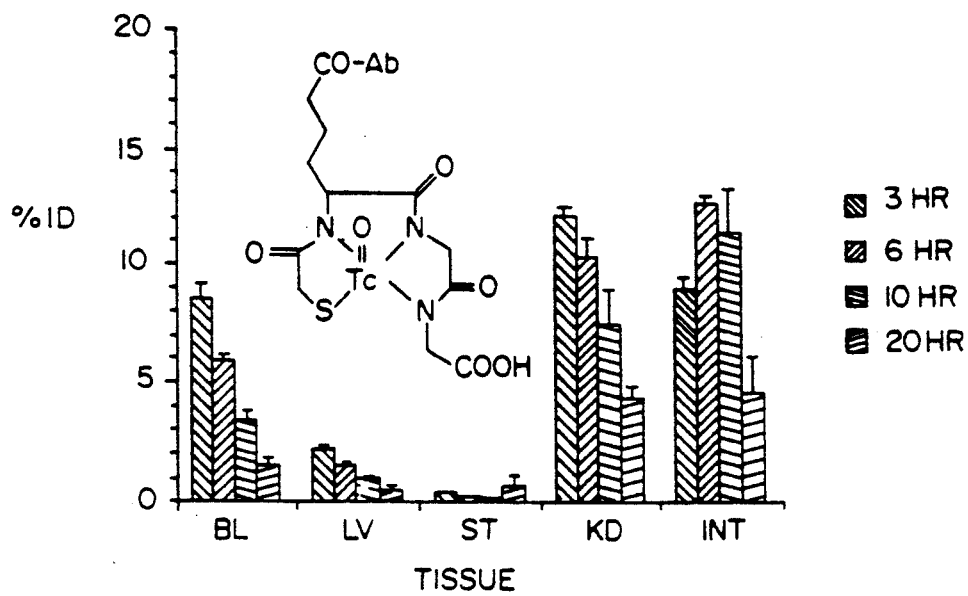
Figure 14B:
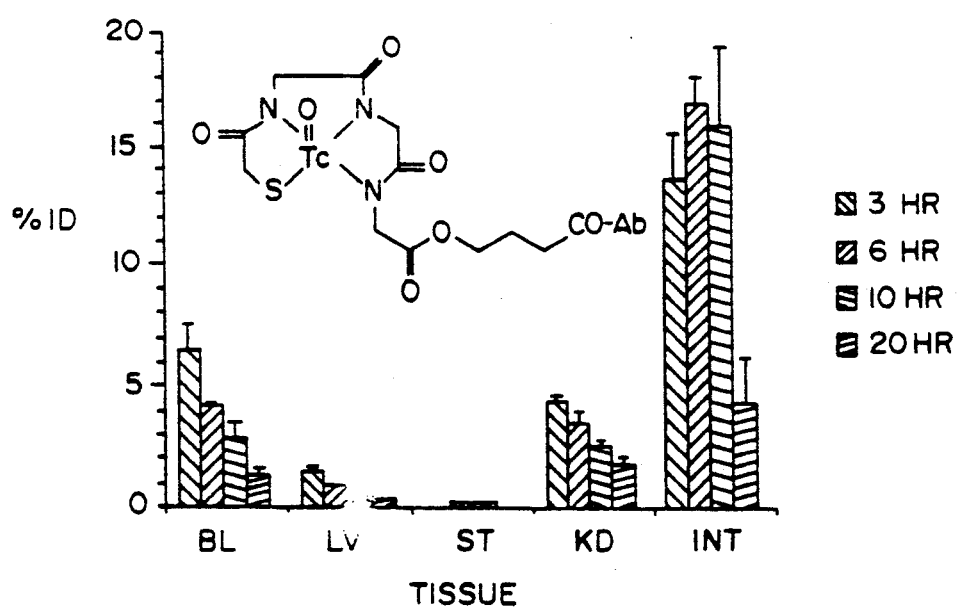

FIG. 14 graphically illustrates biodistribution of $^{99m}$Tc-labeled antibody fragments analyzed in a rat model. The top graph represents biodistribution data for an antibody fragment labeled with a $^{99m}$Tc-N$_3$S chelate wherein there is no ester linkage between the chelate and the antibody. The bottom graph represents biodistribution data for the same antibody fragment labeled with a $^{99m}$Tc-N$_3$S chelate wherein an ester is present in the linkage between the chelate and the antibody, but the ester has an orientation opposite to that of the compounds of the present invention.

Figure 15:
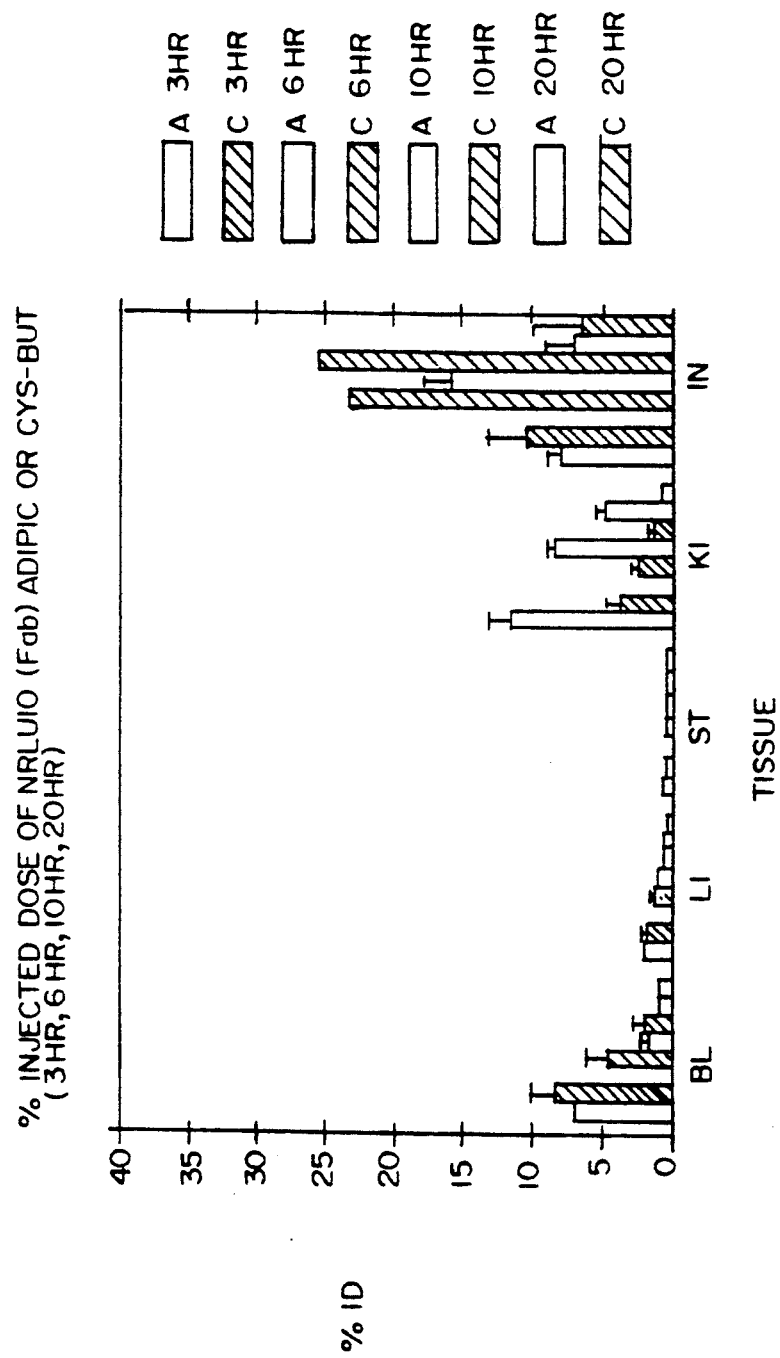

FIG. 15 graphically illustrates biodistribution of $^{99m}$Tc-labeled antibody fragments analyzed in a rat model. The graph represents a composite of biodistribution data for an antibody fragment labeled with a $^{99m}$Tc-N$_3$S chelate wherein there is no ester linkage between the chelate and the antibody, and biodistribution data for the same antibody fragment labeled with a $^{99m}$Tc-N$_3$S chelate wherein an ester is present in the linkage between the chelate and the antibody, but the ester has an orientation opposite to that of the compounds of the present invention.

DETAILED DESCRIPTION OF THE INVENTION

The present invention provides chelating compounds and radionuclide metal chelate compounds prepared therefrom, as well as radiolabeled targeting molecules having the chelates attached thereto. The radionuclide metal chelates of the present invention are attached to targeting molecules such as antibodies to form radiolabeled targeting molecules having diagnostic or therapeutic use. The compounds are bound to a targeting molecule or contain a conjugation group for attachment of the compound to a desired targeting molecule.

Provided by the present invention is a chelating compound of the formula:

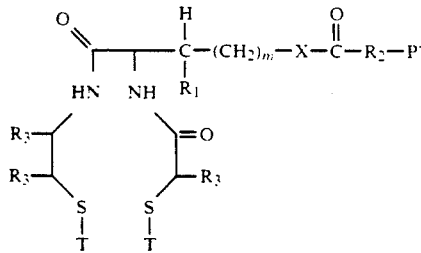

wherein:
m is 0 or 1;
R$_1$ represents H or CH$_3$;
X represents O or S;
each R$_3$ is independently selected from H, CH$_3$, CH$_2$OH, —(CH$_2$)$_n$—CONH$_2$, and —(CH$_2$)$_n$—COOH, wherein n is 0 to about 2, with at least one R$_3$ substituent being —(CH$_2$)$_n$—COOH;
T' and T each represent hydrogen or a sulfur protecting group;
R$_2$ represents a spacer; and
P' represents a targeting molecule or a conjugation group.

R$_2$ may represent any suitable spacer, generally comprising at least one carbon atom, and preferably no more than eight carbon atoms. The spacer should permit both cleaving of the ester (i.e.,

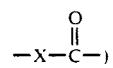

and reaction of a conjugation group P' with a targeting molecule. For example, the R$_2$ spacer should not have a structure that substantially inhibits ester cleavage or the conjugation reaction, e.g., through steric hindrance thereof. Among the suitable R$_2$ spacers for the chelating compounds of the present invention, including those described below, are the following: —(CH$_2$)$_{n'}$— wherein n' is 2-5, preferably 2;

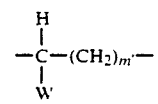

wherein W represents an electron withdrawing group (e.g., a carboxylic acid, SO$_3^-$ or nitro group) or an electron donating group (e.g., a methoxy or hydroxy group) and m' is 1-4;

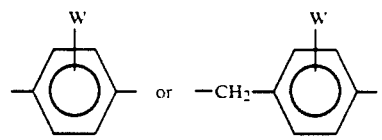

wherein W represents an optional electron donating or withdrawing group.

In one embodiment of the present invention, X is O and R$_2$ is —(CH$_2$)$_2$—. An example of such a chelating compound is the following:

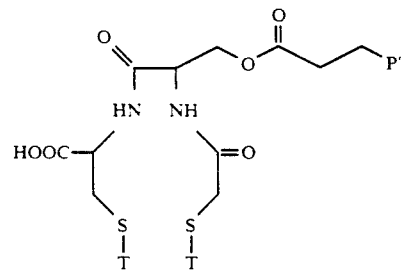

wherein the symbols are as defined above. In one embodiment of the present invention, T represents a hemithioacetal sulfur protecting group such as an ethoxyethyl group, and T' represents an acetamidomethyl sulfur protecting group. These sulfur protecting groups are described below.

Other chelating compounds of the present invention are of the formulas:

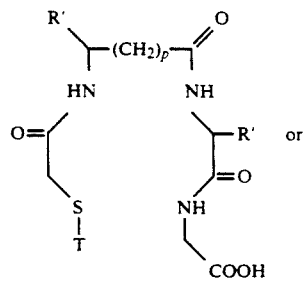

-continued

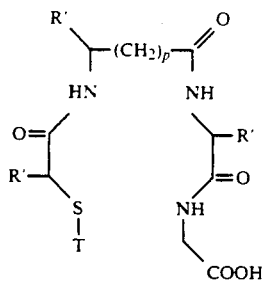

wherein
p is 0 or 1;
one of the R' symbols represents

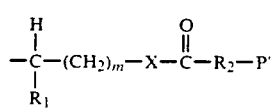

and the others is/are selected from H, CH$_3$, CH$_2$OH, —(CH$_2$)$_n$—CONH$_2$ and —(CH$_2$)$_n$—COOH wherein n is 1 to about 2;
m is 0 or 1;
R$_1$ represents H or CH$_3$;
X represents O or S;
T represents hydrogen or a sulfur protecting group;
R$_2$ represents a spacer; and
P' represents a targeting molecule or a conjugation group.

Other substituents that may be used in positions R' (whichever position is not occupied with the ester-containing linkage terminating in P; are the polar groups —SO$_3^-$, —OSO$_3^-$ —N$^+$(CH$_3$)$_2$, and the like, to further enhance water solubility of the compound.

In one embodiment of the present invention, p is 0, X is O, and R$_2$ is —(CH$_2$)$_2$—. Examples of such chelating compounds are the following:

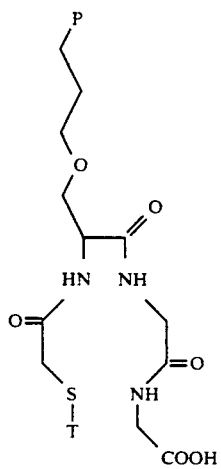

-continued

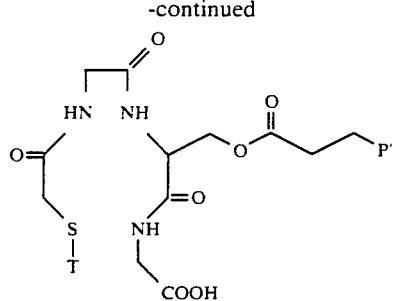

wherein the symbols are as defined above.

Other chelating compounds of the present invention are of the formulas:

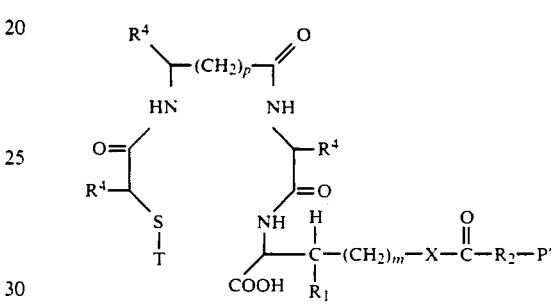

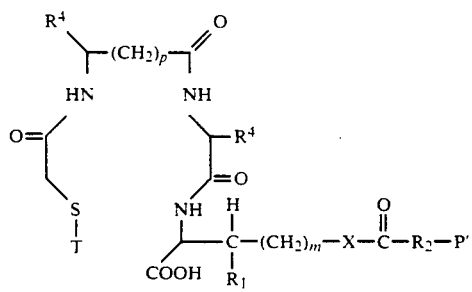

wherein
p is 0 or 1;
each R$_4$ is independently selected from H, CH$_3$, CH$_2$OH, (CH$_2$)$_n$—CONH$_2$, and —(CH$_2$)$_n$—COOH wherein n is 0 to about 2;
m is 0 to about 4, preferably 0 or 1;
R$_1$ represents H or CH$_3$;
X represents O or S;
T represents hydrogen or a sulfur protecting group;
R$_2$ represents a spacer; and
P' represents a targeting molecule or a conjugation group.

Other substituents that may be used in an R$_4$ position are the polar groups —SO$_3^-$, —OSO$_3^-$, —N$^+$(CH$_3$)$_2$, and the like, to further enhance water solubility of the compound.

In one embodiment of the present invention, each R$_4$ is H, p is 0, X is O, and R$_2$ is —(CH$_2$)$_2$—. An example of such a chelating compound is the following:

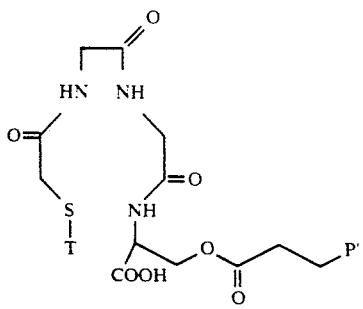

wherein the symbols are as defined above.

Another chelating compound of the present invention is of the formula:

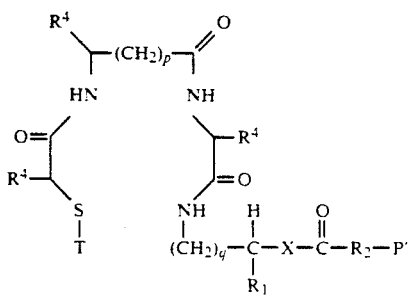

wherein p is 0 or 1;

each $R_4$ is independently selected from H, $CH_3$, $CH_2OH$, $-(CH_2)_n-CONH_2$ and $-(CH_2)_n-COOH$ wherein n is 0 to about 2;

q is 1, 2, or 3;

$R_1$ represents H or $CH_3$;

X represents O or S;

T represents hydrogen or a sulfur protecting group;

$R_2$ represents a spacer; and

P' represents a targeting molecule or a conjugation group.

In one embodiment of the present invention, p is 0, X is O, $R_2$ is $-(CH_2)_2-$, one $R^4$ symbol represents $-(CH_2)_n-COOH$, wherein n is 0 to about 2, and the other $R^4$ symbols represent H. An example of such a chelating compound is the following:

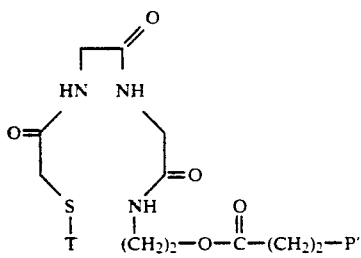

wherein the symbols T and P' are as described above. For one such compound of the present invention, T represents a hemithioacetal sulfur protecting group and P represents an active ester.

The corresponding radionuclide metal chelates are represented by the following formulas, respectively:

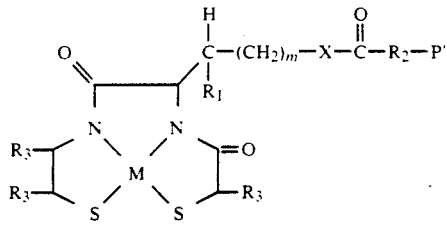

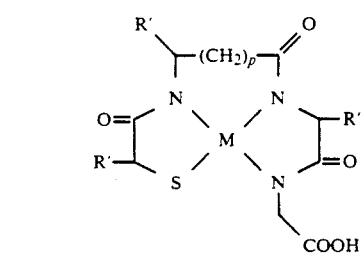

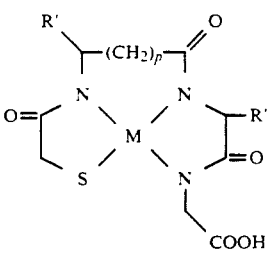

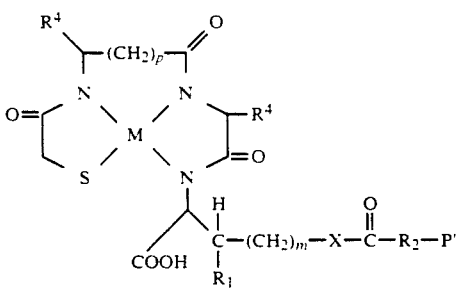

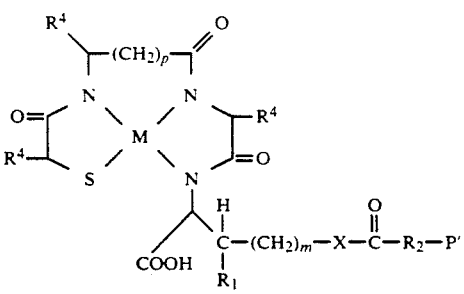

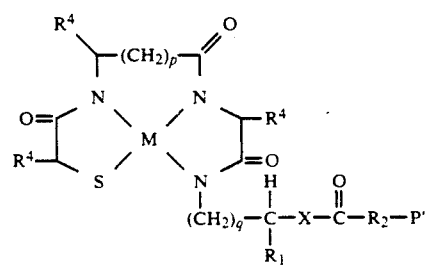

-continued

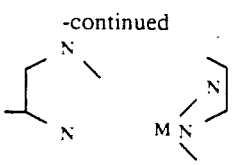

wherein M represents a radionuclide metal or oxide thereof, and the other symbols are as defined above. Stereochemical isomers of these chelates (which form during the radiolabeling reaction) also are encompassed by the present invention.

A conjugation group is a chemically reactive functional group that will react with a targeting molecule to bind the compound thereto. When the targeting molecule is a protein, the conjugation group is reactive under conditions that do not denature or otherwise adversely affect the protein. The conjugation group therefore is sufficiently reactive with a functional group on a protein so that the reaction can be conducted in a substantially aqueous solution and does not have to be forced, e.g. by heating to high temperatures, which may denature the protein. Examples of suitable conjugation groups include but are not limited to active esters, isothiocyanates, amines, hydrazines, maleimides or other Michael-type acceptors, thiols, and activated halides. Among the preferred active esters are N-hydroxysuccinimidyl ester, sulfosuccinimidyl ester, thiophenyl ester, 2,3,5,6- tetrafluoropheny ester, and 2,3,5,6-tetrafluorothiophenyl ester. The latter three preferred active esters may comprise a group that enhances water solubility, at the para (i.e., 4) or the ortho position on the phenyl ring. Examples of such groups are $CO_2H$, $SO_3^-$, $PO_3^{2-}$, $OPO_3^{2-}$, $OSO_3^-$, $N^+R_3$ wherein each R represents H or an alkyl group, and $O(CH_2CH_2O)_nCH_3$ groups.

The targeting molecule is any molecule that will serve to deliver the radionuclide metal chelate to a desired target site (e.g., target cells) in vitro or in vivo. Examples of targeting molecules include, but are not limited to, steroids, cholesterol, lymphokines, and those drugs and proteins that bind to a desired target site.

The targeting molecule may be a targeting protein, which is capable of binding to a desired target site. The term "protein" as used herein includes proteins, polypeptides, and fragments thereof. The targeting protein may bind to a receptor, substrate, antigenic determinant, or other binding site on a target cell or other target site. The targeting protein serves to deliver the radionuclide attached thereto to a desired target site in vivo. Examples of targeting proteins include, but are not limited to, antibodies and antibody fragments, hormones, fibrinolytic enzymes, and biologic response modifiers. In addition, other molecules that localize in a desired target site in vivo, although not strictly proteins, are included within the definition of the term "targeting proteins" as used herein. For example, certain carbohydrates or glycoproteins may be used in the present invention. The proteins may be modified, e.g., to produce variants and fragments thereof, as long as the desired biological property (i.e., the ability to bind to the target site) is retained. The proteins may be modified by using various genetic engineering or protein engineering techniques.

Among the preferred targeting proteins are antibodies, most preferably monoclonal antibodies. A number of monoclonal antibodies that bind to a specific type of cell have been developed, including monoclonal antibodies specific for tumor-associated antigens in humans. Among the many such monoclonal antibodies that may be used are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. The antibody employed in the present invention may be an intact (whole) molecule, a fragment thereof, or a functional equivalent thereof. Examples of antibody fragments are $F(ab')_2$, $Fab'$, $Fab$, and $F_v$ fragments, which may be produced by conventional methods or by genetic or protein engineering.

Targeting molecules are rarely completely specific for a desired target site. Localization in non-target tissues may occur through cross-reactivity or non-specific uptake, for example. In the case of radiolabeled targeting molecules, such localization at non-target sites may result in decreased clarity of diagnostic images (due to the increased "background") and misdiagnosis. Exposure of non-target tissues to radiation also occurs, which is especially undesirable in therapeutic procedures. The improved biodistribution properties of the radiolabeled targeting molecules of the present invention help to alleviate these problems.

The chelating compounds of the present invention comprise either two nitrogen and two sulfur donor atoms or one sulfur and three nitrogen donor atoms, and thus may be termed "$N_2S_2$" or "$N_3S$" chelating compounds, respectively. The radiolabeled targeting proteins of the present invention exhibit certain improved biodistribution properties compared to targeting proteins radiolabeled with certain other $N_2S_2$ or $N_3S$ chelates. Most notably, localization of radioactivity within the intestines and kidneys is reduced.

Targeting proteins radiolabeled with certain $N_2S_2$ radionuclide metal chelates are described, for example, in European patent application publication No. 188,256 as well as co-pending U. S. patent applications Ser. Nos. 07/065,011 now U.S. Pat. No. 4,847,255 and 07/367,502. The use of $N_3S$ chelates to radiolabel proteins is described in European patent application publication No. 284,071. When the radiolabeled proteins disclosed in these previous patent applications are administered in vivo, a percentage of the injected dosage of the radionuclide becomes localized within the intestines (i.e., becomes part of the intestinal contents, rather than binding to intestinal epithelial tissue per se) and/or the kidneys. Although stable attachment of radionuclides to antibodies and effective localization thereof on target tumors has been achieved using these previous protein radiolabeling systems, reduction of the localization of radioactivity in non-target organs would be a desired improvement. U.S. patent application Ser. No. 07/367,502 embodies one approach for reducing non-target organ localization of radioactivity, but further mitigation of this problem would be beneficial.

In these earlier approaches, a portion of the non-target-bound administered radiolabeled proteins (e.g., antibodies or fragments thereof) most likely is first metabolized to produce radiolabeled catabolites that subsequently enter the intestines, probably through hepatobiliary excretion. When the chelate is attached to lysine residues of the targeting protein, a major catabolite appears to be the lysine adduct of the chelate. Intestinal localization of radioactivity may be confused with (or obstruct) target sites in the abdominal area. For therapeutic procedures, the dosage that can be safely administered is reduced when intestinal localization occurs (due to exposure of normal tissues to the radiation). The therapeutic effect on the target sites therefore also is reduced.

As illustrated in the examples below, the biodistribution patterns in vivo differ when targeting proteins (e.g., antibody fragments) are radiolabeled with a chelate of the present invention, compared to radiolabeling using certain other $N_3S$ and $N_2S_2$ chelates. The advantage of reduced intestinal and kidney localization is demonstrated for the radiolabeled targeting proteins of the present invention. While not wishing to be bound by theory, it is believed that the improved biodistribution properties of the radiolabeled proteins of the invention are at least in part attributable to the presence and orientation of a cleavable ester within the linkage joining the chelate to the protein. The chemical structure of the chelating compounds and the resulting stereochemistry of the chelates released by cleavage of the linker also may play a role in reducing localization of radioactivity in the intestines and kidneys.

The ester component of the linkage between the chelate core and the protein is cleavable at the position indicated by the arrow:

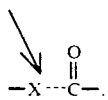

Cleaving of the ester in vivo is believed to occur due to hydrolysis, chemical elimination, and/or enzymatic cleavage (e.g., by liver or kidney esterases), or a combination thereof. However, the conjugates of the present invention have demonstrated sufficient stability in serum for in vivo use.

After cleavage of the ester, the portion of the linkage still attached to the chelate terminates in a hydroxyl group (when X is O) or a sulfhydryl group (when X is S). The orientation of the ester

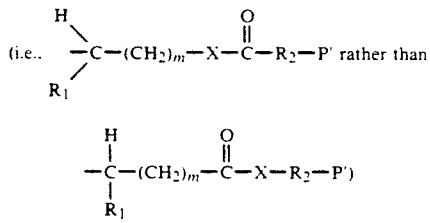

also appears to be beneficial for achieving the desired biodistribution properties. The relatively small size of the chelate released by ester cleavage (compared, for example, to the above-described lysine adduct catabolites) may also contribute to the efficient clearance of radioactivity from the body. Lysine adducts of the chelates may be a minor metabolite of the radiolabeled proteins of the present invention.

The carboxylic acid substituent(s) on the compounds of the present invention increase the polarity, and therefore the water solubility, of the compounds. The increased water solubility is believed to further contribute to decreased hepatobiliary uptake of the radiolabeled proteins or catabolites thereof. Other substituents that enhance polarity (e.g., a sulphonate group) may be used on the chelating compounds, in addition to (or instead of) the COOH substituents. The free carboxylic acid substituent(s) also may assist in the chelation of the radionuclide, thereby promoting good radiolabeling yields.

The chelating compounds of the present invention may be synthesized using amino acid derivatives. The various compounds within the scope of the present invention may be prepared by choosing amino acids having the desired side chains to produce the different $R_3$, $R_4$ and other substituents, and other structural variations. For example, when $R_1$ is hydrogen, m is 0, and X is O, the cleavable ester is within a serine derivative. (The hydroxyl of serine is believed to be generated upon cleavage of the ester.) When $R_1$ is $-CH_3$, m is 0, and X is O, the linkage is a threonine derivative. When $R_1$ is hydrogen, m is 0, and X is S, the linkage is a cysteine derivative. When m is 1, the linkage may be considered to be a homo derivative of the amino acids (homoserine, homothreorine, and homocysteine, respectively.)

The use of natural amino acids may contribute to recognition of the ester-containing linkage by esterases in vivo. Amino acids having side chains that enhance polarity and therefore water solubility (e.g., $-COOH$ and $-CH_2OH$) also are generally desirable, and may be used to vary the $R_3$ and $R_4$ substituents, for example.

During radiolabeling, bonds form between the four donor atoms and the radionuclide metal to form the corresponding radionuclide metal chelate. Any suitable conventional sulfur protecting group(s) may be attached to the sulfur donor atoms of the compounds of the present invention. The protecting groups should be removable, either prior to or during the radiolabeling reaction. In the case of $N_2S_2$ compounds, the protecting groups attached to the two sulfur donor atoms may be the same or different. Alternatively, a single protecting group, e.g. a thioacetal group, may protect both sulfur donor atoms. Among the preferred sulfur protecting groups are acetamidomethyl and hemithioacetal protecting groups, which are displacable from the chelating compound during the radiolabeling reaction.

An acetamidomethyl sulfur-protecting group is represented by the following formula, wherein the sulfur atom shown is a sulfur donor atom of the chelating compound:

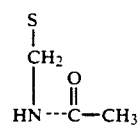

The acetamidomethyl group is displaced from the chelating compound during radiolabeling conducted at about 50° C. in a reaction mixture having a pH of about 3 to 6.

When hemithioacetal protective groups are used, each sulfur atom to be protected has a separate protective group attached to it, which together with the sulfur atom defines a hemithioacetal group. The hemithioacetal groups contain a carbon atom bonded directly (i.e., without any intervening atoms) to a sulfur atom and an oxygen atom, i.e.,

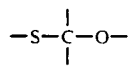

Preferred hemithioacetals generally are of the following formula, wherein the sulfur atom is a sulfur atom of the chelating compound, and a separate protecting group is attached to each of the sulfur atoms on the chelating compound:

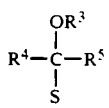

wherein $R^3$ is a lower alkyl group, preferably of from two to five carbon atoms, and $R^4$ is a lower alkyl group, preferably of from one to three carbon atoms. Alternatively, $R^3$ and $R^4$ may be taken together with the carbon atom and the oxygen atom shown in the formula to define a nonaromatic ring, preferably comprising from three to seven carbon atoms in addition to the carbon and oxygen atoms shown in the formula. $R^5$ represents hydrogen or a lower alkyl group wherein the alkyl group preferably is of from one to three carbon atoms. Examples of such preferred hemithioacetals include, but are not limited to:

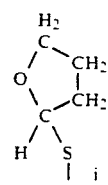
Tetrahydrofuranyl

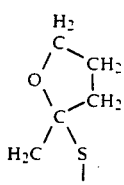
2-methyl tetrahydrofuranyl

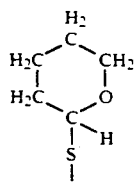
Tetrahydropyranyl

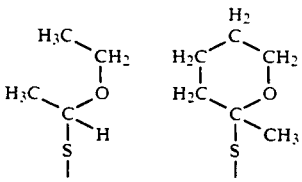
ethoxyethyl    2-methyl tetrahydropyranyl

Other hemithioacetal sulfur protecting groups include those derived from monosaccharides, such as the following, wherein the sulfur atom is a sulfur donor atom of the chelating compound:

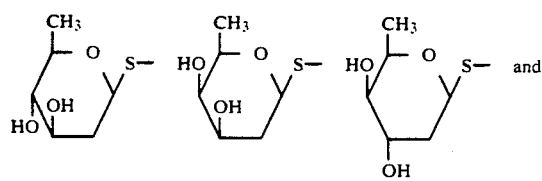

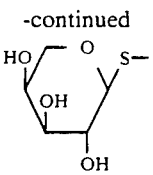

These sulfur-protective groups are displaced during the radiolabeling reaction, conducted at acidic pH, in what is believed to be metal-assisted acid cleavage. Bonds form between the sulfur atoms and the metal radionuclide. A separate step for removal of the sulfur-protective groups is not necessary. The radiolabeling procedure thus is simplified. In addition, the basic pH conditions and harsh conditions associated with certain known radiolabeling procedures or procedures for removal of other sulfur protective groups are avoided. Thus, base-sensitive groups on the chelating compound survive the radiolabeling step intact. Such base labile groups include any group which may be destroyed, hydrolyzed, or otherwise adversely affected by exposure to basic pH. In general, such groups include esters, maleimides, and isothiocyanates, among others. Such groups may be present on the chelating compound as protein conjugation groups.

The chelating compounds of the present invention are radiolabeled, using conventional procedures, with any of a variety of radionuclide metals to form the corresponding radionuclide metal chelates. These radionuclide metals include, but are not limited to, copper (e.g., $^{67}$Cu and $^{64}$Cu); technetium (e.g., $^{99m}$Tc); rhenium (e.g., $^{186}$Re and $^{188}$Re); lead (e.g., $^{212}$Pb); bismuth (e.g., $^{212}$Bi); palladium (e.g., $^{109}$Pd), and rhodium (e.g., $^{105}$Rh). Methods for preparing these isotopes are known. Molybdenum/technetium generators for producing $^{99m}$Tc are commercially available. Procedures for processing $^{186}$Re include the procedures described by Deutsch et al., (*Nucl. Med. Biol.* Vol. 13:4:465-477, 1986) and Vanderheyden et al. (*Inorganic Chemistry.* Vol. 24:1666-1673, 1985), and methods for production of $^{188}$Re have been described by Blachot et al. (*Intl. J. of Applied Radiation and Isotopes* Vol. 20:467-470, 1969) and by Klofutar et al. (*J. of Radioanalytical Chem.*, Vol. 5:3-10, 1970). Production of $^{109}$Pd is described in Fawwaz et al., *J. Nucl. Med.* (1984), 25:796. Production of $^{212}$Pb and $^{212}$Bi is described in Gansow et al., *Amer. Chem. Soc. Symp. Ser.* (1984), 241:215-217, and Kozah et al., *Proc. Nat'l. Acad. Sci.* USA (January 1986) 83:474-478. $^{99m}$Tc is preferred for diagnostic use, and the other radionuclides listed above have therapeutic use.

In one embodiment of the present invention, chelating compounds of the invention comprising acetamidomethyl and/or hemithioacetal sulfur protective groups are radiolabeled with a metal radionuclide by reacting the compound with the radionuclide under conditions of acidic pH. It is believed that the acidic pH and the presence of the metal both contribute to the displacement of the sulfur protective groups from the chelating compound. The radionuclide is in chelatable form when reacted with the chelating compounds of the invention.

In the case of technetium and rhenium, being in "chelatable form" generally requires a reducing step. A reducing agent will be employed to reduce the radionuclides (e.g., in the form of pertechnetate and perrhenate, respectively) to a lower oxidation state at which chelation will occur. Many suitable reducing agents, and the use thereof, are known. (See, for example, U.S. Pat. Nos. 4,440,738; 4,434,151; and 4,652,440.) Such reducing agents include, but are not limited to, stannous ion (e.g., in the form of stannous salts such as stannous chloride or stannous fluoride), metallic tin, ferrous ion (e.g., in the form of ferrous salts such as ferrous chloride, ferrous sulfate, or ferrous ascorbate) and many others. Sodium pertechnetate (i.e., $^{99m}TcO_4-$ which is in the +7 oxidation level) or sodium perrhenate (i.e., $^{188}ReO_4-$, $^{186}ReO_4-$) may be combined simultaneously with a reducing agent and a chelating compound of the invention in accordance with the radiolabeling method of the invention, to form a chelate.

Preferably, the radionuclide is treated with a reducing agent and a complexing agent to form an intermediate complex (i.e., an "exchange complex"). Complexing agents are compounds which bind the radionuclide more weakly than do the chelate compounds of the invention, and may be weak chelators. Any of the suitable known complexing agents may be used, including but not limited to gluconic acid, glucoheptonic acid, methylene disphosphonate, glyceric acid, glycolic acid, tartaric acid, mannitol, oxalic acid, malonic acid, succinic acid, bicine, malic acid, N,N'-bis(2-hydroxy ethyl) ethylene diamine, citric acid, ascorbic acid and gentisic acid. Good results are obtained using gluconic acid or glucoheptonic acid as the technetium-complexing agent and citric acid for rhenium. When the radionuclide in the form of such an exchange complex is reacted with the chelating compounds of the invention, the radionuclide will transfer to these compounds which bind the radionuclide more strongly to form chelates of the invention. Heating is often required to promote transfer of the radionuclide. Radionuclides in the form of such exchange complexes also are considered to be in "chelatable form" for the purposes of the present invention.

Chelates of $^{212}Pb$, $^{212}Bi$, $^{103}Rh$, and $^{109}Pd$ may be prepared by combining the appropriate salt of the radionuclide with the chelating compound and incubating the reaction mixture at room temperature or at higher temperatures. It is not necessary to treat the lead, bismuth, rhodium, palladium, and copper radioisotopes with a reducing agent prior to chelation, as such isotopes are already in an oxidation state suitable for chelation (i.e., in chelatable form). The specific radiolabeling reaction conditions may vary somewhat according to the particular radionuclide and chelating compound involved.

The chelating compound may be radiolabeled to form a radionuclide metal chelate, which then is reacted with a targeting protein. Alternatively, the unlabeled chelating compound may be attached to the targeting protein and subsequently radiolabeled. For the second approach, sulfur protecting group(s) that are displaceable/removable at a pH compatible with the presence of a protein should be used. Among the protecting groups suitable for use in the second approach are acyl type groups such as those of the formula

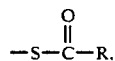

wherein the S is a sulfur atom of the chelating compound and R is an alkyl or aryl group. Examples are S-isobutyryl, S-benzoyl, and S-acetyl protecting groups.

Proteins contain a variety of functional groups; e.g., carboxylic acid (COOH) or free amine (—NH$_2$), groups, which are available for reaction with a suitable protein conjugation group on a chelator to bind the chelator to the protein. For example, an active ester on the chelator reacts with epsilon amine groups on lysine residues of proteins to form amide bonds. Alternatively, a targeting molecule and/or a chelator may be derivatized to expose or attach additional reactive functional groups. The derivatization may involve attachment of any of a number of linker molecules such as those available from Pierce Chemical Company, Rockford, Illinois. (See the Pierce 1986-87 General Catalog, pages 313-54.) Alternatively, the derivatization may involve chemical treatment of the protein (which may be an antibody). Procedures for generation of free sulfhydryl groups on antibodies or antibody fragments are also known. (See U.S. Pat. No. 4,659,839.) Maleimide conjugation groups on a chelator are reactive with the sulfhydryl (thiol) groups.

Alternatively, when the targeting molecule is a carbohydrate or glycoprotein, derivatization may involve chemical treatment of the carbohydrate; e.g., glycol cleavage of the sugar moiety of a glycoprotein antibody with periodate to generate free aldehyde groups. The free aldehyde groups on the antibody may be reacted with free amine or hydrazine conjugation groups on the chelator to bind the chelator thereto. (See U.S. Pat. No. 4,671,958.)

The radiolabeled targeting molecules of the present invention have use in diagnostic and therapeutic procedures, both for in vitro assays and for in vivo medical procedures. The radiolabeled molecules may be administered intravenously, intraperitoneally, intralymphatically, locally, or by other suitable means, depending on such factors as the type of target site. The amount to be administered will vary according to such factors as the type of radionuclide (e.g., whether it is a diagnostic or therapeutic radionuclide), the route of administration, the type of target site(s), the affinity of the targeting molecule for the target site of interest, and any cross-reactivity of the targeting molecule with normal tissues. Appropriate dosages may be established by conventional procedures and a physician skilled in the field to which this invention pertains will be able to determine a suitable dosage for a patient. A diagnostically effective dose is generally from about 5 to about 35 and typically from about 10 to about 30 mCi per 70 kg body weight. A therapeutically effective dose is generally from about 20 mCi to about 300 mCi. For diagnosis, conventional noninvasive procedures (e.g., gamma cameras) are used to detect the biodistribution of the diagnostic radionuclide, thereby determining the presence or absence of the target sites of interest (e.g., tumors).

To render the ester in the conjugates of the present invention more susceptible to cleavage in the kidneys, an agent that raises urine pH may also be administered to the patient. Such agents include, for example, a salt of ascorbate (e.g., sodium ascorbate) or a bicarbonate salt (e.g., sodium bicarbonate), which may be administered intravenously. Raising the urine pH to a basic level promotes cleavage of the ester in conjugates or catabolites thereof localized in the kidneys. Clearance of the released radionuclide metal chelates from the body is thereby enhanced. Administration of such agents to promote cleavage of ester linkers in vivo is described in U.S. patent application Ser. No. 07/251,900, which is hereby incorporated by reference.

The comparatively low intestinal localization of the therapeutic radiolabeled antibodies of the present invention or catabolites thereof permits increased dosages, since intestinal tissues are exposed to less radiation. The clarity and accuracy of diagnostic images also is improved by the reduced localization of radiolabeled antibodies or catabolites thereof in normal tissues.

The following examples are presented to illustrate certain embodiments of the present invention.

Example 1

Synthesis of serine succinate reagent 6

Figure 1:
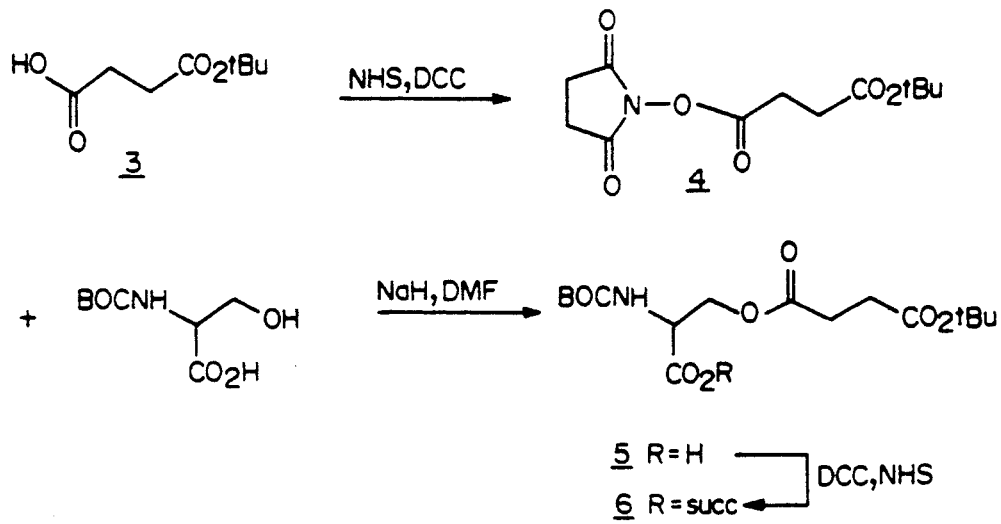
FIGS. 1-10 and 16 depict chemical synthesis procedures that may be used to prepare certain chelating compounds of the present invention.

The synthesis procedure is generally as depicted in FIG. 1.

t-butyl, succinimidyl succinate 4 (LG694-73): To an ice cold solution of succinic acid mono-t-butyl ester 3 (870 mg, 5.0 mmol) and NHS (630 mg, 5.5 mmol) in acetonitrile (7.0 mL) was added DCC (1130 mg, 5.5 mmol). The reaction was allowed to warm to room temperature and stirred for 4.5 hours. The reaction was cooled to 0° C., treated with 0.1 mL acetic acid, and filtered. The filtrate was evaporated to give a gummy solid (1280 mg, theoretical yield). $^1$H NMR (CDCl$_3$): 1.40 (s, 9H), 2.60 (t, 2H), 2.80 (s, 4H), 2.90 (t, 2H).

serinyl succinate 5 (LG694-97): To an ice cold suspension of sodium hydride (60 mg, 2.49 mmol) in DMF (1.0 mL), was added a solution of N-BOC serine (170 mg, 0.83 mmol). The suspension was stirred for 30 minutes and then treated with a solution of 4 (225 mg, 0.83 mmol) in DMF (1.0 mL). The suspension was warmed to room temperature and stirred for 16 hours. The reaction was quenched at 0° C. by the addition of a solution of acetic acid (0.1 mL) in EtOAc (1.0 mL). The suspension was partitioned between EtOAc and pH 4.0 buffer. The aqueous was extracted with EtOAc (2×30 mL). The aqueous was acidified to pH 1.0 with 1.0 M HCl and further extracted with EtOAc (30 mL). The combined EtOAc extracts were washed with brine, dried, and evaporated to give an oil. Chromatography afforded 5 as a colorless oil (190 mg, 0.53 mmol, 53%). $^1$H NMR (CDCl$_3$): 1.40 (2 overlapping singlets, 18H), 2.55 (broad s, 4H), 4.40-5.50 (m, 2H), 4.60 (broad s, 1H), 5.50 (broad d, 1H). MS m/e (rel intensity): 362 (M+H, 13), 337 (22), 250 (52), 154 (100).

serinyl succinate NHS ester 6 (LG694-79): To an ice cold solution of 5 (600 mg, 1.66 mmol) and NHS (229 mg, 1.99 mmol) in acetonitrile (2.5 mL) was added DCC (394 mg, 1.91 mmol). The reaction was warmed to room temperature and stirred for 2 hours. The reaction was cooled to 0° C., treated with acetic acid (0.1 mL), and filtered. The filtrate was evaporated to give 6 as an oil (760 mg, 1.66 mmol, theoretical yield). $^1$H NMR (CDCl$_3$): 1.45 (2 overlapping singlets, 18H), 2.55-2.70 (m, 4H), 2.85 (s, 4H), 4.55 (dd, 2H), 5.05 (broad s, 1H), 5.60 (broad d, 1H).

Example 2

Synthesis of cysteine-serine succinate 13

Figure 2:
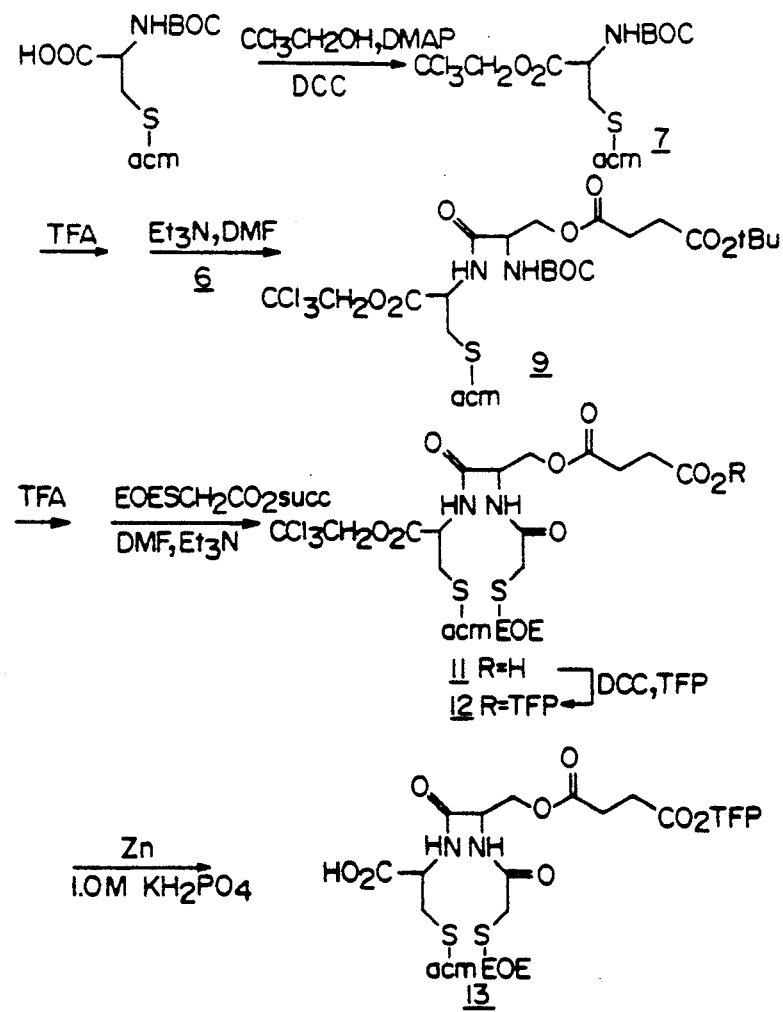

The procedure is generally as depicted in FIG. 2. S-acm-N-tBOC cysteine TCE ester 7 (JRW 443-14): DCC (794 mg, 3.85 mmol) was added to a solution of S-acm-N-tBOC cysteine (966 mg, 3.50 mmol) and N,N-dimethyl aminopyridine (47 mg, 0.385 mmol) in trichloroethanol (0.37 mL, 3.85 mmol) and acetonitrile (18 mL). The suspension was stirred at room temperature for 48 hours. The suspension was filtered. The filtrate was evaporated. The residue was dissolved in EtOAc (75 mL) and washed with saturated NaHCO$_3$ (2×50 mL). The EtOAc was dried, evaporated to give an oil which was crystallized from ether/hexanes to give 7 as a white solid (500 mg, 1.22 mmol, 35%). $^1$H NMR (CDCl$_3$) 1.50 (s, 9H), 2.05 (s, 3H), 3.10 (dd, 2H), 4.40-4.60 (m, 2H), 4.60-4.95 (overlapping dd and s, 3H), 5.70 (broad d, 1H), 6.90 (broad s, 1H). M.p. 76° C.-77° C.

cys-ser-succinate 9 (LG 694-80): To an ice cold solution of 7 (772 mg, 1.66 mmol) in CH$_2$Cl$_2$ (3.0 mL), was added trifluoroacetic acid (4.0 mL). The reaction was warmed to room temperature and stirred for 1 hour. The solution was coevaporated with carbon tetrachloride (3×30 mL). The residue (8) was dissolved in DMF (1.5 mL), cooled to 0°, and treated with triethylamine (0.24 mL, 1.72 mmol). To this solution was added a solution of 6 (760 mg, 1.66 mmol) in DMF (1.5 mL). To this was added triethylamine 0.48 mL, 3.32 mmol). The reaction was warmed to room temperature and stirred for 16 hours. The solution was diluted with EtOAc (50 mL) and washed with 0.1 M HCl, brine, dried, and evaporated to give an oil (1.4 g). The oil was chromatographed (50% EtOAc:Hexanes 1% HOAc, 700 mL, then 75% EtOAc:Hexanes 1% HOAc, then 99:1 EtOAc:HOAc, 200 mL) to give 9 as an oil (200 mg, 0.30 mmol, 18%). $^1$H NMR (CDCl$_3$): 1.50 (overlapping singlets, 18H), 2.05 (s, 3H), 2.55 (broad s, 4H), 3.15 (dd, 2H), 4.40-4.65 (m, 5H), 4.70-5.05 (overlapping broad s, dd 3H), 5.70 (broad d, 1H), 6.85 (broad s, 1H), 7.75 (broad d, 1H). MS m/e (rel intensity): 668 (M+2, 5), 666 (M, 5), 568 (11), 510 (19), 439 (25), 57 (100).

cysteine-ser-succ SEOE ma 11 (LG694-81): To an ice cold solution of 9 (200 mg, 0.30 mmol) in CH$_2$Cl$_2$ (2.0 mL), was added trifluoroacetic acid (2.0 mL). The solution was stirred at room temperature for 1 hour. The solution was coevaporated with carbon tetrachloride (3×30 mL). The residue was dissolved in DMF (0.5 mL) and cooled to 0°. To this solution was added triethylamine (42 μL, 0.30 mmol). To this was added S-ethoxyethyl mercaptoacetic acid succinimidyl ester 42 (94 mg, 0.36 mmol) and triethylamine (84 μL, 0.60 mmol). The ice bath was allowed to melt and the reaction was stirred at room temperature for 18 hours. The solution was diluted with EtOAc (50 mL) and washed with pH 4.0 buffer. The aqueous was extracted with EtOAc (25 mL). The combined EtOAc extracts were washed with brine, dried, and evaporated to give an oil. The oil was chromatographed (23 mm column, 1:1 EtOAc:Hexanes 1% HOAc, 400 mL, then 99:1 EtOAc:HOAc, 700 mL, and lastly 10% IPA EtOAc 1% HOAc) to give 11 as a foam (80 mg, 0.12 mmol, 41%). $^1$H NMR:1.25 (t, 3H), 1.50 (d, 3H), 2.05 (s, 3H), 2.50-2.70 (m, 4H), 3.30 (m, 2H), 3.40-4.30 (m, 5H), 4.35-4.95 (m, 8H), 6.90 (broad s, 1H), 7.55-7.65 (broad t, 1H), 7.90-8.05 (broad t, 1H). MS m/e : 678 (M+Na), 610, 391, 149.

TFP ester 12 (LG694-82): To an ice cold solution of 11 (55 mg, 0.08 mmol) in THF (0.50 mL), were added tetrafluorophenol (18 mg, 0.11 mmol) and DCC (19 mg, 0.10 mmol). The ice bath was removed and the solution was stirred at room temperature for 18 hours. The mixture was cooled to 0°, treated with acetic acid (0.1 mL), and filtered. The filtrate was evaporated to give an oil. The oil was chromatographed (1:1 EtOAc:Hexanes 1% HOAc, 200 mL, then 99:1 EtOAc:HOAc, 200 mL) to give 12 as an oil (45 mg, 0.055 mmol, 70%). $^1$H NMR (CDCl$_3$): 1.20-1.35 (m, 3H), 1.55 (d, 3H), 2.10 (s, 3H), 2.85 (t, 2H), 3.05-3.15 (m, 4H), 3.40 (m, 2H), 3.50-3.85 (m, 2H), 4.35-5.05 (m, 9H), 6.70 (broad s, 1H), 6.90-7.15

(m, 1H), 6.90–7.15 (m, 1H), 7.70 (m, 1H), 8.20 (broad s, 1H). MS m/e (rel intensity): 806 (M+2, 14), 804 (M, 12), 761 (64), 759 (52), 735 (35), 733 (28), 689 (37), 687 (37) 663 (42), 436 (41), 410 (50), 155 (100).

cys-ser succinate 13 (LG 694-85): To a solution of 12 (30 mg, 0.037 mmol) in THF (0.4 mL) and 1.0 M $KH_2PO_4$ (80 μL) was added zinc dust (39 mg, 0.59 mmol). After 1 hour, additional 1.0 M $KH_2PO_4$ (80 μL) and zinc dust (39 mg, 0.59 mmol) were added. The mixture was agitated in a sonicator for 2 hours. The mixture was filtered, rinsed with acetonitrile and 50% $CH_3CN/H_2O$ 1% HOAc. The filtrate was evaporated. The residue was chromatographed (10% IPA:$CH_2Cl_2$ 1% HOAc, 50 mL, then 25% IPA:$CH_2Cl_2$ 2% HOAc) to give 13 as a foam (14 mg, 0.02 mmol, 57%). $^1H$ NMR ($CDCl_3$): 1.25 (t, 3H), 1.60 (d, 3H), 2.05 (s, 3H), 2.85 (t, 2H), 3.10 (m, 4H), 3.35 (m, 2H), 3.40–3.80 (m, 2H), 4.30–5.00 (m, 9H), 6.65 (m, 1H), 6.90–7.10 (m, 1H), 7.70 (m, 1H), 8.20 (broad s, 1H). An alternative and preferred procedure for synthesizing chelating compound 13 is presented in example 11.

Example 3

Synthesis of $N_3S$ serine succinate 20

Figure 3:
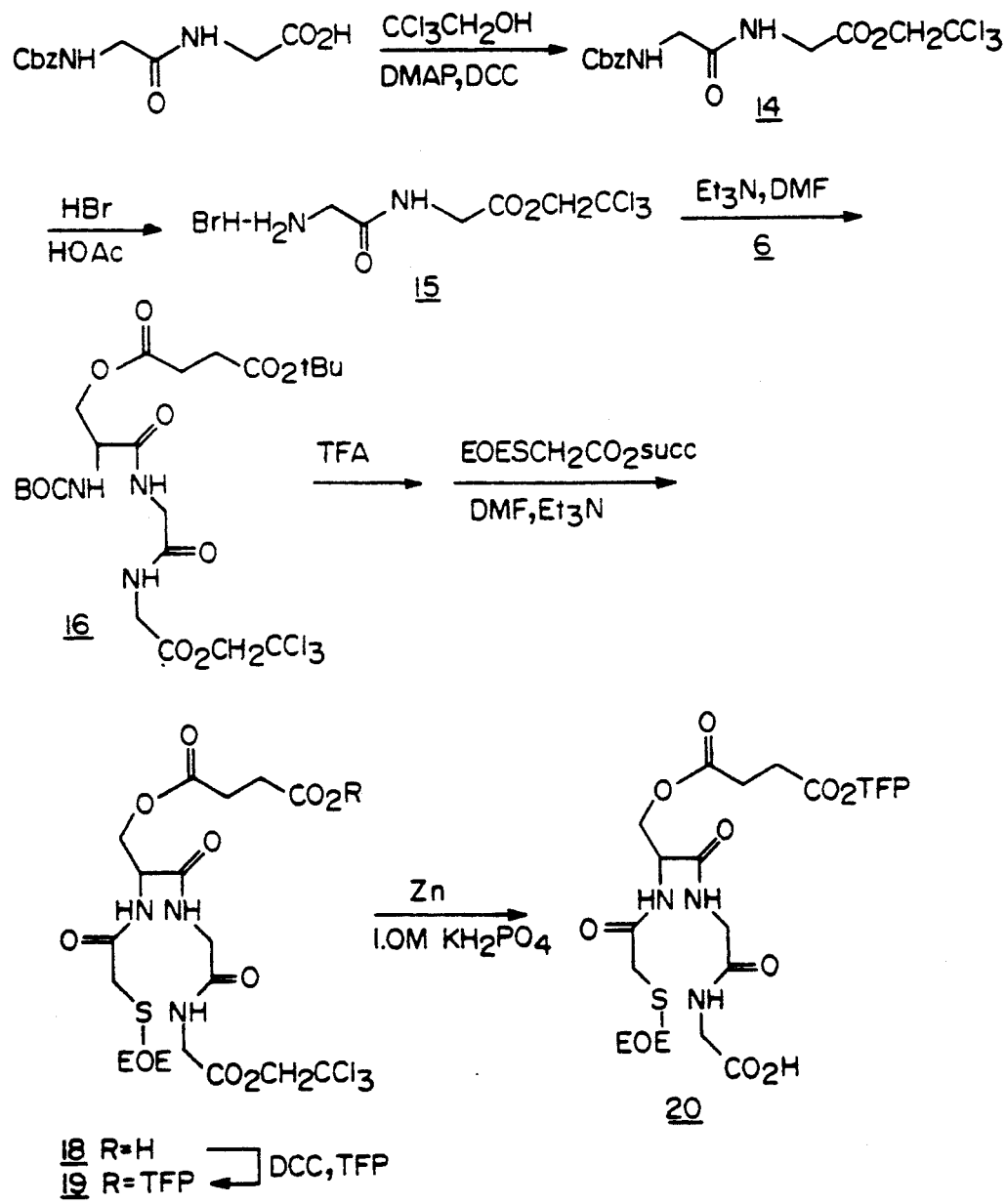

The procedure is generally as depicted in FIG. 3. N-Cbz-gly-gly TCE ester 14 (LG694-99): To a suspension of N-Cbz-gly-gly (2.00 g, 7.52 mmol) in acetonitrile (35.0 mL) was added trichloroethanol (0.94 mL). To this suspension was added 4-dimethylaminopyridine (1.107 g, 9.02 mmol). The solution was stirred for 10 minutes and then treated with DCC (1.86 g, 9.02 mmol). The mixture was stirred for 18 hours. The mixture was filtered. The filtrate was evaporated. The residue was dissolved in EtOAc (50 mL) and washed with saturated $NaHCO_3$ (50 mL). The aqueous was extracted with EtOAc (2×30 mL). The combined EtOAc extracts were washed with brine, dried and evaporated to give an oil. The oil was crystallized from EtOAc/Hexanes to give 14 as a white solid (2.44 g, 6.16 mmol, 82%). $^1H$ NMR ($CDCl_3$): 3.95 (d, 2H), 4.20 (d, 2H), 4.80 (s, 2H), 5.15 (s, 2H), 5.50 (broad s, 1H), 6.70 (broad s, 1H), 7.35 (s, 5H).

gly-gly TCE ester 15 (LG762-4): A suspension of 14 (1.60 g, 4.0 mmol) in acetic acid (16 mL) was gently heated to complete dissolution of 14. To this solution was added dropwise 30% HBr/HOAc (16 mL). The mixture was kept at room temperature for 2 hours and then diluted with $Et_2O$ and evaporated. The residue was evaporated twice from heptane and then diluted with $Et_2O$. The mixture was filtered. The solid was collected by filtration and dried in vacuo, to give 15 as a white solid (1.37 g, 4.0 mmol, theoretical yield). $^1H$ NMR (DMSO): 3.65 (broad d, 2H), 4.15 (d, 2H), 4.95 (s, 2H), 8.00 (broad s, 1H), 8.90 (broad t, 1H).

N-BOC-T-Butyl ester 16 (LG762-3): To an ice cold solution of 15 (656 mg, 1.91 mmol) and 6 (797 mg, 1.74 mmol) in DMF (7.0 mL), was added triethylamine (0.36 mL, 2.60 mmol). The ice bath was allowed to melt and the reaction was stirred at room temperature for 18 hours. The solution was evaporated. The residue was dissolved in EtOAc (50 mL) and washed with pH 4.0 buffer. The aqueous was extracted with EtOAc (2×25 mL). The combined EtOAc extracts were washed with brine, dried, and evaporated to give an oil. The oil was chromatographed (1:1 EtOAc:Hexanes 1% HOAc, 120 mL, then 99:1 EtOAc:HOAc, 200 mL) to give 16 as a white foam (720 mg, 1.19 mmol, 68%). $^1H$ NMR ($CDCl_3$): 1.50 (s, 18H), 2.60 (s, 4H), 4.10 (m, 2H), 4.20 (d, 2H), 4.40–4.60 (m, 3H), 4.80 (s, 2H), 5.75 (broad d, 1H), 7.20–7.40 (m, 2H).

ser-succinic acid 18 (LG762-5): To an ice cold solution of 16 (360 mg, 0.59 mmol) in $CH_2Cl_2$ (2.0 mL) was added trifluoroacetic acid (2.0 mL). The reaction was warmed to room temperature and stirred for 1 hour. The solution was coevaporated with carbon tetrachloride (3×20 mL). The residue, 17, was rinsed with $Et_2O$ and dried. The residue was dissolved in DMF (2.0 mL), cooled to 0°, and treated with S-ethoxyethyl mercaptoacetic acid succinimidyl ester 42 (186 mg, 0.71 mmol). To this was added triethylamine (0.21 mL, 1.48 mmol). The ice bath was allowed to melt and the reaction was stirred at room temperature for 18 hours. The solution was poured into EtOAc (40 mL) and washed with pH 4.0 buffer. The aqueous was extracted with EtOAc (30 mL). The aqueous was acidified to pH 1.0 with 1.0 M HCl, and extracted with EtOAc (2×30 mL). The combined EtOAc extracts were washed with brine, dried, and evaporated to give an oil. The oil was chromatographed (99:1 EtOAc:HOAc) to give 18 as a foam (200 mg, 0.33 mmol, 56%). $^1H$ NMR ($CDCl_3$): 1.20 (td, 3H), 1.55 (dd, 3H), 2.65 (s, 4H), 3.35 (dd, 2H), 3.45–3.80 (m, 2H), 3.90–4.60 (m, 7H), 4.70–4.85 (m, 3H), 7.40–7.70 (m, 3H).

TFP ester 19 (LG762-6): To a solution of 18 (200 mg, 0.33 mmol) and tetrafluorophenol (83 mg, 0.49 mmol) in acetonitrile (1.20 mL) was added DCC (83 mg, 0.40 mmol). The mixture was stirred at room temperature for 18 hours. The mixture was cooled to 0° and filtered. The filtrate was evaporated. The residue was chromatographed (75% EtOAc:Hexanes 1% HOAc) and gave 19 as an oil (150 mg, 0.20 mmol, 61%). $^1H$ NMR ($CDCl_3$): 1.25 (td, 3H), 1.55 (dd, 3H), 2.85 (t, 2H), 3.05 (t, 2H), 3.30 (m, 2H), 3.40–3.80 (m, 2H), 3.95–4.10 (m, 2H), 4.20 (d, 2H), 4.40–4.90 (m, 6H), 6.90–7.20 (m, 2H), 7.20–7.35 (m, 1H), 7.50–7.70 (m, 1H).

$N_3S$ acid 20 (LG762-7): To a solution of 19 (150 mg, 0.20 mmol) in THF (1.30 mL) and 1.0 M $KH_2PO_4$ (0.27 mL) was added zinc dust (138 mg, 2.12 mmol). The reaction mixture was stirred for 40 minutes. Additional 1.0 M $KH_2PO_4$ (0.27 mL) and zinc dust (138 mg, 2.12 mmol) were added. The mixture was stirred for 1 hour and then agitated in a sonicator for 25 minutes. The mixture was filtered through Celite, rinsed with acetonitrile, and 40% $CH_3CN/H_2O$ 1% HOAc. The filtrate was evaporated. The residue was chromatographed (15% IPA:$CH_2Cl_2$ 1% HOAc) and gave 20 as a white foam (48 mg, 0.08 mmol, 39%). $^1H$ NMR: 1.10 (t,3H), 1.45 (d, 2H) 2.70 (t, 2H), 3.05 (t, 2H), 3.20–3.40 ($H_2O$ in DMSO), 3.60–3.80 (m, 3H), 4.10–4.35 (m, 4H), 4.60–4.85 (m, 2H), 7.70–8.10 (m, 1H), 8.20–8.50 (m, 2H).

Example 4

Preparation of Radionuclide Metal Chelates and Attachment of the Chelates to Targeting Proteins $^{99m}Tc$ Chelates: Chelating compounds 13 and 20, synthesized in Examples 1-3, were both radiolabeled with $^{99m}Tc$ according to the following procedures:

Method A

One mL of sterile water for injection was added to a sterile vial containing a stannous gluconate complex (50 mg sodium gluconate and 1.2 mg stannous chloride dihydrate, available from Merck Frosst, Canada, in dry solid form lyophilized at pH 6.1–6.3) and the vial was gently agitated until the contents were dissolved. A sterile insulin syringe was used to inject 0.1 mL of the resulting stannous gluconate solution into an empty sterile vial. Sodium pertechnetate (1.0 mL, 75-100 mCi, eluted from a $^{99}$Mo/$^{99}$Tc generator purchased from DuPont, Mediphysics, Mallinckrodt or E.R. Squibb) was added, and the vial was agitated gently to mix the contents, then incubated at room temperature for 1-2 minutes to form a $^{99m}$Tc-gluconate complex.

Method B

In an alternative procedure for providing the $^{99m}$Tc-gluconate exchange complex, the kit includes a vial containing a lyophilized preparation at pH 1.8 with sulfuric acid comprising 2.5 mg sodium gluconate, 0.10 mg stannous chloride dihydrate, 0.1 mg gentisic acid as a stabilizer compound, and about 40 mg lactose as a filler compound to aid in lyophilization. One mL of sodium pertechnetate (about 100 mCi) was added directly to the lyophilized preparation. The vial was agitated gently to mix the contents to form the $^{99m}$Tc-gluconate complex.

A separate vial containing 0.3 mg of a chelating compound in dry solid form was prepared by dispensing a solution of 0.3 mg chelating compound (either compound 13 or 20 in acetonitrile into the vial, then removing the solvent under $N_2$ gas. To this vial was then added 0.9 mL of 100% isopropyl alcohol, and the vial was gently shaken for about 2 minutes to completely dissolve the chelating compound. Next, 0.6 mL of this solution of the chelating compound was transferred to a vial containing 0.16 mL of glacial acetic acid/0.2 N HCl (2:14), and the vial was gently agitated. Of this acidified solution, 0.5 mL was transferred to the vial containing the $^{99m}$Tc-gluconate complex, prepared in Method A above. To the Tc-gluconate complex prepared in Method B, 0.1 mL of the chelating compound in isopropanol (1.0 mg/mL) and 0.4 mL isopropanol were added. After thorough agitation to mix, the vials from both Methods A and B were incubated in a 75° C.±2° C. water bath for 15 minutes to form the $^{99m}$Tc-chelate, then immediately transferred to a 0° C. ice bath for 2 minutes.

The Fab fragment of a monoclonal antibody (10 mg in 0.5 mL of PBS) was generated by treating the monoclonal antibody with papain according to conventional techniques. The monoclonal antibody, designated NR-LU-10, recognizes a pancarcinoma antigen. Other proteins may be substituted for the NR-LU-10 Fab fragment.

Either of the vials containing the acidified solution of the $^{99m}$Tc-labeled chelate (see above) was removed from the ice bath, 2.0 mL of 250 mM sodium bicarbonate buffer pH 9.3 was added, and the vial was agitated to mix. Immediately, the antibody solution (above) was added, gently agitated to mix and incubated at room temperature for 10 minutes to allow conjugation of the radiolabeled chelate to the antibody.

A column containing an anion exchanger, either DEAE-Sephadex or QAE-Sephadex, was used to purify the conjugate. The column was prepared under aseptic conditions as follows. Five 1 mL QAE-Sephadex columns were connected end-to-end to form a single column. Alternatively, a single 5 mL QAE-Sephadex column may be used. The column was washed with 5 mL of 37 mM sodium phosphate buffer, pH 6.8. A 1.2μ filter (available from Millipore) was attached to the column, and a 0.2 μ filter attached to the 1.2 μ filter. A 22-gauge sterile, nonpyrogenic needle was attached to the 0.2μ filter.

The reaction mixture was drawn up into a 5 mL syringe, and any air bubbles were removed from the solution. After removal of the needle, the syringe was connected to the QAE-Sephadex column on the end opposite the filters. The needle cap was removed from the 22-gauge needle attached to the filter end of the column and the needle tip was inserted into a sterile, nonpyrogenic test tube. Slowly, over 2 minutes, the reaction mixture was injected into the column. The eluant was collected into a sterile, nonpyrogenic 10 mL serum vial. The now empty syringe on top of the column was replaced with a 5 mL syringe containing 5 mL of 150 mM (0.9%) sodium chloride solution (from which air bubbles had been removed). Slowly, over 2 minutes, the NaCl solution was injected into the column, and the eluent was collected in the serum vial. The radiolabeled antibody fragments were thus recovered from the reaction mixture.

$^{188}$Re Chelates

The same chelating compounds may be radiolabeled with $^{188}$Re by a procedure similar to the $^{99m}$Tc labeling procedure. Sodium perrhenate produced from a W-188/Re-188 research scale generator is combined with citric acid (a preferred complexing agent for $^{188}$Re), a reducing agent, and preferably gentisic acid and lactose. The resulting $^{188}$Re-citrate exchange complex is heated with the desired chelating compound, as above. A $C_{18}$ reversed phase low pressure material (Baker $C_{18}$ cartridges) may be used to purify the $^{188}$Re-chelate. A monoclonal antibody or fragment thereof is reacted with the chelate in a buffered solution to bind the chelate thereto, as described for the $^{99m}$Tc procedure. A Sephadex G-25 column may be used to purify the radiolabeled antibody.

Example 5

Preparation of Chelating Compound 28

Figure 4:
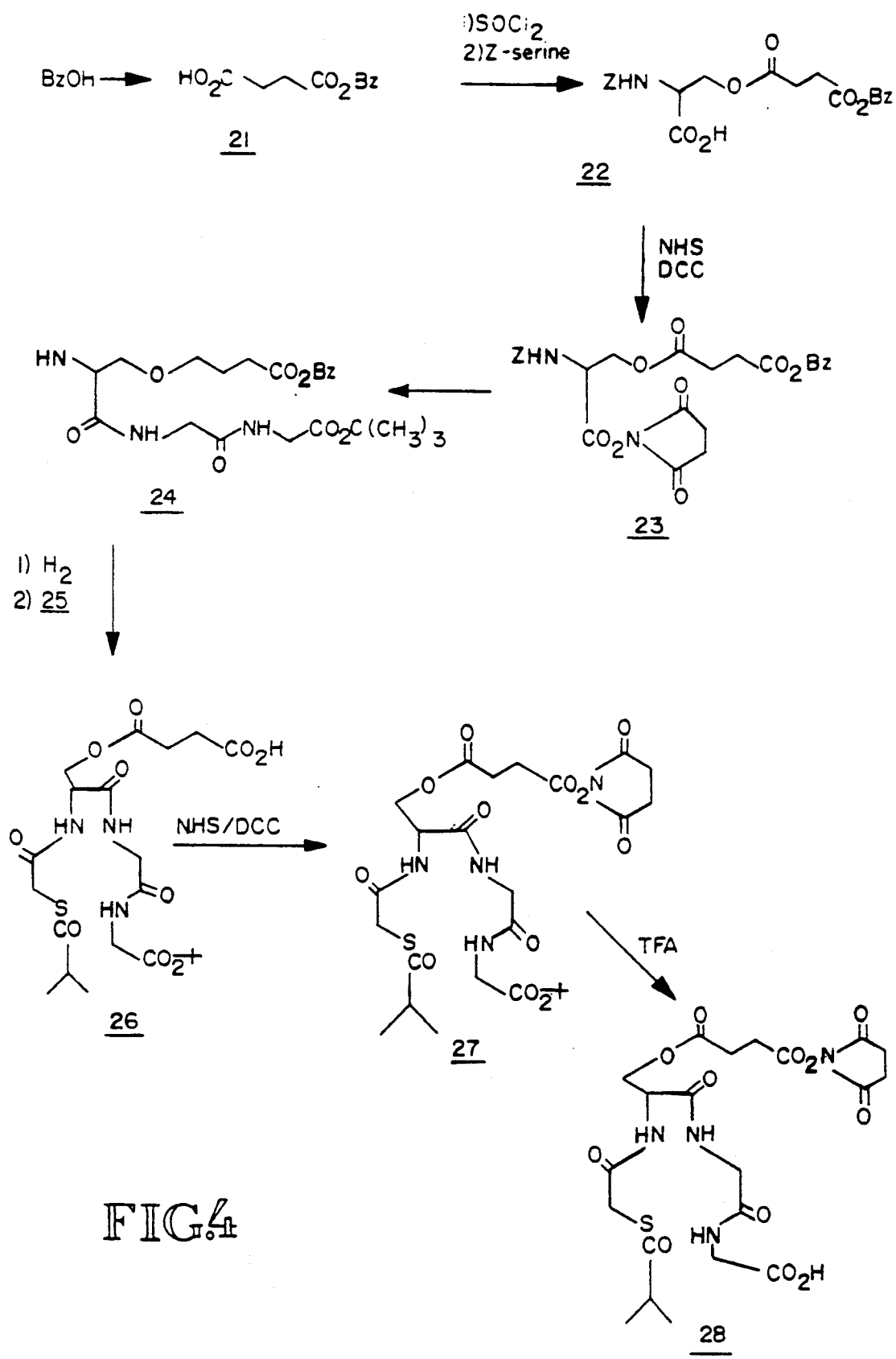

The procedure is generally as shown in FIG. 4.

Butanedioic acid monobenzylester 21

To a solution of 4.13 mL (4.32 g, 40 mmol) of benzyl alcohol and 4.40 g (44 mmol) of succinic anhydride in 100 mL of THF at 0° C. was added at once 12.24 mL (8.90 g, 88 mmol) of $Et_3N$. The mixture was allowed to come to room temperature and stirred for 18 h at which time it was concentrated under vacuum to a viscous oil and partitioned between 100 mL of 1 N HCl and 100 mL of EtOAc. The EtOAc layer was extracted with 84 mL of 5% $NaHCO_3$ solution. The aqueous layer was acidified with concentrated HCl solution to pH 1 and extracted with two 50 mL portions of EtOAc. The EtOAc layers were combined and washed with brine, dried ($MgSO_4$), filtered, and concentrated to give 6.9 g (83%) of 21 as a white chunky solid: $^1$H NMR ($CDCl_3$) 2.70 (s, 4H), 5.22 (s, 2H), 7.38 (s, 5H).

O-(3-Carbobenzoxypropanoyl)-N-Cabobenzoxyserine) 22

To a solution of 4.08 g (19.6 mmol) of 21 in 20 mL of $CH_2Cl_2$ was added 2.14 mL (3.50 g, 29.4 mmol) of $SOCl_2$. The mixture was stirred at room temperature for 6 h and concentrated under vacuum. The resulting yellow oil was dissolved in 20 mL of $CH_2Cl_2$, and the solution was cooled to 0° C. To the mixture was added 4.96 g (19.6 mmol) of N-carbobenzoxyserine, 3.17 mL (3.10 g, 39.2 mmol) of pyridine, and 244 mg (2.0 mmol) of N,N-dimethyl-4-aminopyridine. The mixture was allowed to warm to room temperature, stirred for 16 h, and partitioned between 100 mL of EtOAc and 100 mL of 1 N HCl. The HCl layer was washed with 50 mL of EtOAc and the combined EtOAc layers were washed with brine, dried (MgSO$_4$), filtered, and concentrated to give 9.08 g of viscous yellow oil. Purification by chromatography on silica gel (75% EtOAc/25% hexanes/1% HOAc) gave 7.68 g (91%) of 22 as a viscous oil: $^1$H NMR (CDCl$_3$) 2.54–2.71 (m, 4H), 4.30–7.72 (m, 3H), 5.09 (s,2H), 5.11 (s, 2H), 5.78 (m, 1H), 7.31 (s, 10H).

O-(3-Carbobenzoxypropanoyl)-N-carbobenzoxyserine N'hydroxysuccinimidyl ester, 23

To a solution of 1.60 g (3.73 mmol) of 22 in 20 mL of CH$_3$CN at 0° was added 471 mg (4.09 mmol) of N-hydroxysuccinimde followed by 1.15 g (5.59 mmol) of N,N$^1$-dicyclohexylcarbodiimide. The mixture was stirred at 0° for 1 h and placed in the freezer for 16 h. To the mixture was added 200 μL of HOAc, and the mixture was placed back in the freezer for an additional 2 h. The solids were removed by filtration, and the filtrate was concentrated to give a viscous oil containing white solid. Purification by chromatography on silica gel (40% EtOAc/60% hexanes/1% HOAc) gave 1.34 g (68%) of 23 as a viscous oil: $^1$H NMR (CDCl$_3$) 2.71 (s, 4H), 2.80 (s, 4H), 4.40–4.72 (m, 3H) 5.08 (s, 2H), 5.12 (s, 2H), 5.80 (m, 1H), 7.31 (s, 10H).

O-(3-Carbobenzoxypropanoyl)-N-carbobenzoxyseryl-glycylglysine O-t-butyl ester, 24

To a suspension of 355 mg (1.58 mmol) of glycylglycine O-t-butyl ester hydrochloride [prepared as described by Moore et al JCS(C) 2349, 1966] in a solution of 756 mg (1.43 mmol) of 23 in 2.8 mL of DMF at 0° was added at once 472 μL (4.34 mg, 4.29 mmol) of N-methylmorpholine. The mixture was stirred for 2 h at 0° and partitioned between 10 mL of 1N HCl and 2×20 mL of EtOAc. The combined EtOAc layers were washed with sat NaCl, dried (MgSO$_4$), filtered, and concentrated to give an oil which was purified by chromatography on silica gel (80% EtOAc/20% hexanes) to give 460 mg (54%) of 24 as a sticky gum: $^1$H NMR (DMSO) 1.41 (s, 9H), 2.58 (m, 4H), 3.75 (m, 4H), 4.03–4.52 (m, 3H), 5.05 (s, 2H), 5.10 (s, 2H), 7.36 (s, 10H), 7.66 (d, 1H), 8.15 (t, 1H), 8.39 (t, 1H).

S-Isobutrylmercaptoacetic acid N-hydroxysuccinimidyl ester 25

To a solution of 61 mg (0.47 mmol) of CoCl$_2$ in 20 mL of acetonitrile under nitrogen atmosphere was added dropwise over 5 minutes, a solution of 4.92 mL (5.0 g, 47 mmol) of isobutryl chloride and 2.97 mL (3.94 g, 43 mmol) of mercaptoacetic acid in 50 mL of acetonitrile. The mixture was stirred at room temperature for 2 hours and concentrated under vacuum. The resulting blue oil was partitioned between 50 mL of 0.1 N HCl and 100 mL of ether. The ether layer was washed with brine and concentrated to give an oil. Purification by silica gel chromatography (26% ethyl acetate, 4% acetic acid, 70% hexanes) yielded 3.30 g (47%) of S-isobutrylmercaptoacetic acid as an oil: $^1$H NMR (CDCl$_3$): δ 1.23 (d, 6H), 2.84 (m, 1H), 3.85 (s, 2H).

To a solution of 3.30 g (20 mmol) of the above acid in 100 mL of methylene chloride at 0° C. was added 2.53 g (22 mmol) of N-hydroxysuccinimide followed by 4.52 g (22 mmol) of N,N'-dicyclohexylcarbodiimide. The mixture was allowed to stir for 16 hours allowing the ice bath to equilibrate to room temperature. The mixture was chilled and filtered through celite. The filtrate was concentrated and purified by silica gel chromatography (50% EtOAc-50% hexanes) to give 4.48 g of 25 as a viscous oil: $^1$H NMR (CDCl$_3$) δ 1.23 (d, 6H), 2.80 (m, 1H), 2.81 (s, 4H), 3.98 (s, 2H).

N-(S-Isobutyrylmercaptoacetyl)-(O-3-carboxy-propanoyl)servlglycylglysine O-t-butyl ester 26

A 250 mL hydrogenation flask was charged with 460 mg (0.77 mmol) of 24, 7.7 mL of methanol, and 77 mg of 10% palladium on charcoal. The mixture was shaken under 60 psi of H$_2$ for 2 h, filtered, and concentrated to give 260 mg of a glassy solid. This material was dissolved in 2.0 mL of DMF and cooled to 0°, and to the mixture was added 216 mg (0.83 mmol) of 25 and 91 μL (84 mg, 0.83 mmol) of N-methylmorpholine. The mixture was stirred for 2 h at 0°, and 0.5 mL of acetic acid was added. The mixture was concentrated under vacuum to about 0.5 mL and purified by chromatography on silica gel (96% HOAc/4% HOAc) to give 250 mg of a mixture of 26 [$^1$H NMR (CDCl$_3$) 1.21 (d, 6H), 1.48 (s, 9H), 2.55–3.10 (m, 5H), 3.61 (m, 2H), 3.95 (m, 4H), 4.70–4.87 (m, 3H), 6.88 (m, 1H), 7.40 (m, 2H)] and impurities identified to be N-hydroxysuccinimide, DMF, and acetic acid by NMR. By NMR integration the yield of 26 was determined to be 151 mg (45%). Compound 26 was used as is in the following step.

N-Hydroxysuccinimidyl ester of compound 26, 27

To a solution of 151 mg (0.31 mmol) of 26 and 36 mg (0.31 mmol) of additional NHS in 1.5 mL of CH$_2$Cl$_2$ was added 128 mg (0.62 mmol) of N,N'-dicyclohexylcarbodiimide. The mixture was stirred for 3 h at room temperature, 3 drops of acetic acid were added, and the mixture stirred for an additional 1 h. The mixture was filtered and concentrated to an oil which was purified by silica gel chromatography (7.5/92.5/1, isopropyl alcohol/CH$_2$Cl$_2$/HOAc) and triturated with Et$_2$O to give 120 mg (63%) of 27 as a white solid: $^1$H NMR (DMSO) 1.13 (d, 6H), 1.41 (s, 9H), 2.68 (t, 2H), 2.82 (s, 4H), 2.93 (t, 2H), 2.60–3.0 (buried m, 1H), 3.70 (s, 2H), 3.78 (m, 4H), 4.22 (m, 2H), 4.61 (m, 1H), 8.16 (t, 1H), 8.46 (m, 2H).

N-(S-Isobutyrylmercaptoacetyl)-O-(3-carbo-N'-hydroxysuccinimidylpropanoyl)-servlglycylglycine 28

To a solution of 120 mg (0.19 mmol) of 27 in 750 μL of CH$_2$Cl$_2$ was added 750 μL of trifluoroacetic acid. The resulting solution was stirred for 1.5 h, concentrated under vacuum, and triturated twice with Et$_2$O to give 110 mg of 28 as a white solid. Purification of 30 mg by C$_{18}$ reversed phase HPLC (25% CH$_3$CN/75% H$_2$O/1% HOAc) yielded 13 mg of pure 28 which was used for making conjugates: $^1$H NMR (DMSO) 1.12 (d, 6H), 2.68 (t, 2H), 2.80 (s, 4H), 2.92 (t, 2H), 2.50–3.00 (buried m, 1H), 3.68 (s, 2H), 3.76 (m, 4H), 4.20 (m, 2H), 4.60 (m, 1H), 8.10 (t, 1H), 8.41 (m, 2H).

EXAMPLE 6

Synthesis of Chelating Compound 33

Figure 5:
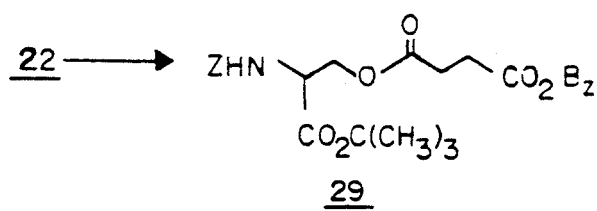
Figure 5:
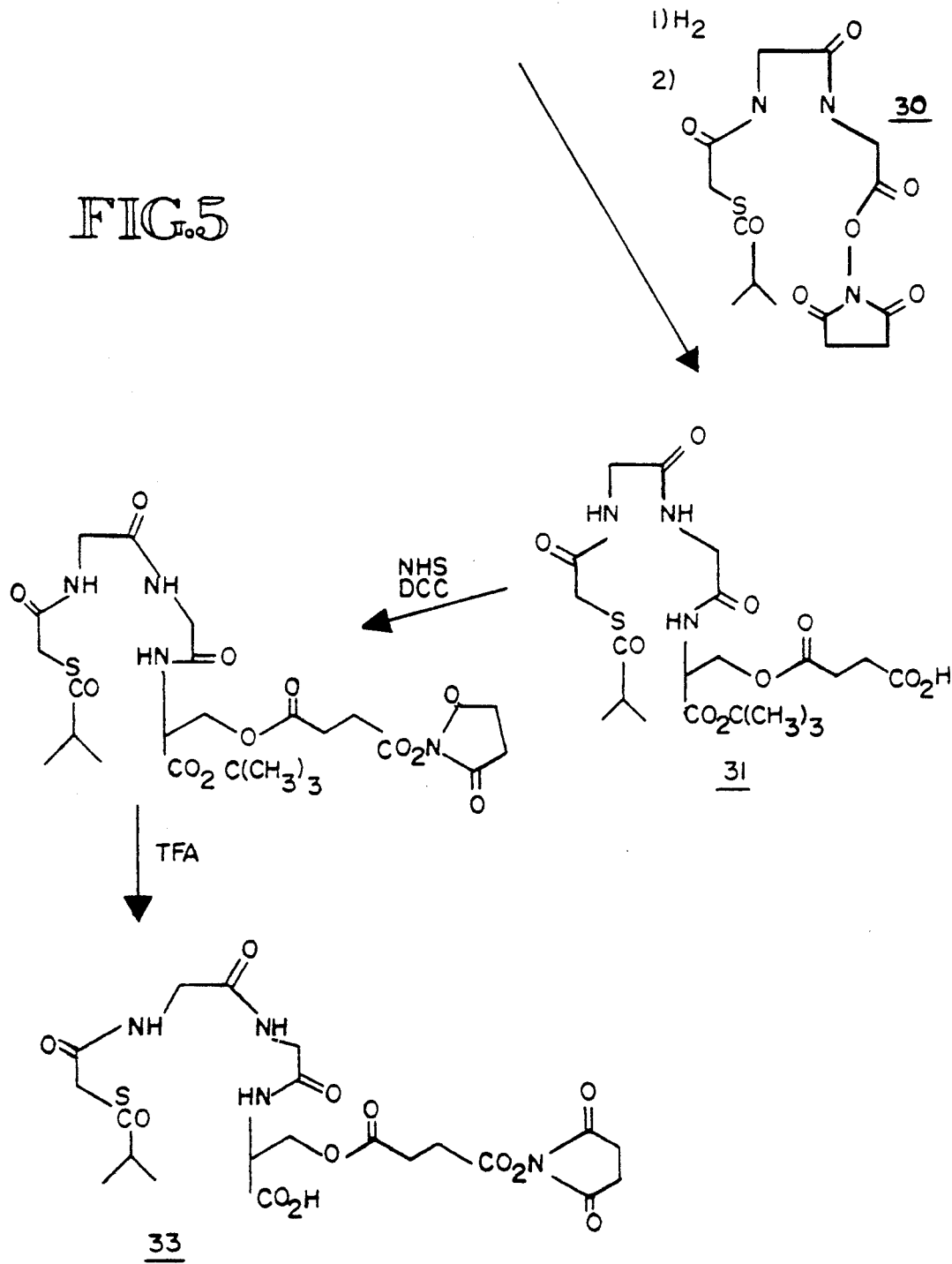

The procedure is generally as depicted in FIG. 5. Compound 22 can be esterified with isobutylene to provide t-butyl ester 29 which can be hydrogenated to remove the benzyl ester and the benzyl carbamate protecting groups. Acylation of the deprotected amino group with compound 30 (prepared analogously to 44 using 25 instead of 42) can provide 31. Analogously to the previous example, compound 31 can be converted to compound 33 by forming the NH ester and removing the t-butyl ester to provide 33.

EXAMPLE 7

Preparation of Protein Conjugate 34

To a solution of 262 μL (5 mg, 1×10$^{-4}$ mmol) of 19 mg/mL Fab fragment of a monoclonal Ab (NRML-05) and 738 μL of pH 7.5 buffer (100 mM sodium phosphates, 150 mM sodium chloride) was added over 5 seconds with rapid mixing 7.4 μL (0.112 mg, 2×10$^{-4}$ mmol) of a 15 mg/mL solution of 28 in DMSO. The mixture was gently mixed to ensure mixing for 1 h, and the conjugated protein 34 was isolated by size exclusion chromatography (PD-10 Sephadex G-25M) eluting with degassed phosphate buffered saline (PBS) to give a 2 mL fraction which contained 3.92 mg of protein as evidenced by UV absorbance at 280 nm. Isoelectric focusing showed an anodal shift indicating that the protein had been modified by increasing the net negative charge on the protein. Offering larger aliquots of ligand showed larger anodal shifts. The conjugate was concentrated to a concentration of 4 mg/mL by centrifugal concentration (Centricon-10).

EXAMPLE 8

Deprotection of Conjugate to Provide Free Sulfhydryl Chelating Compound Conjugate 35

Figure 6:
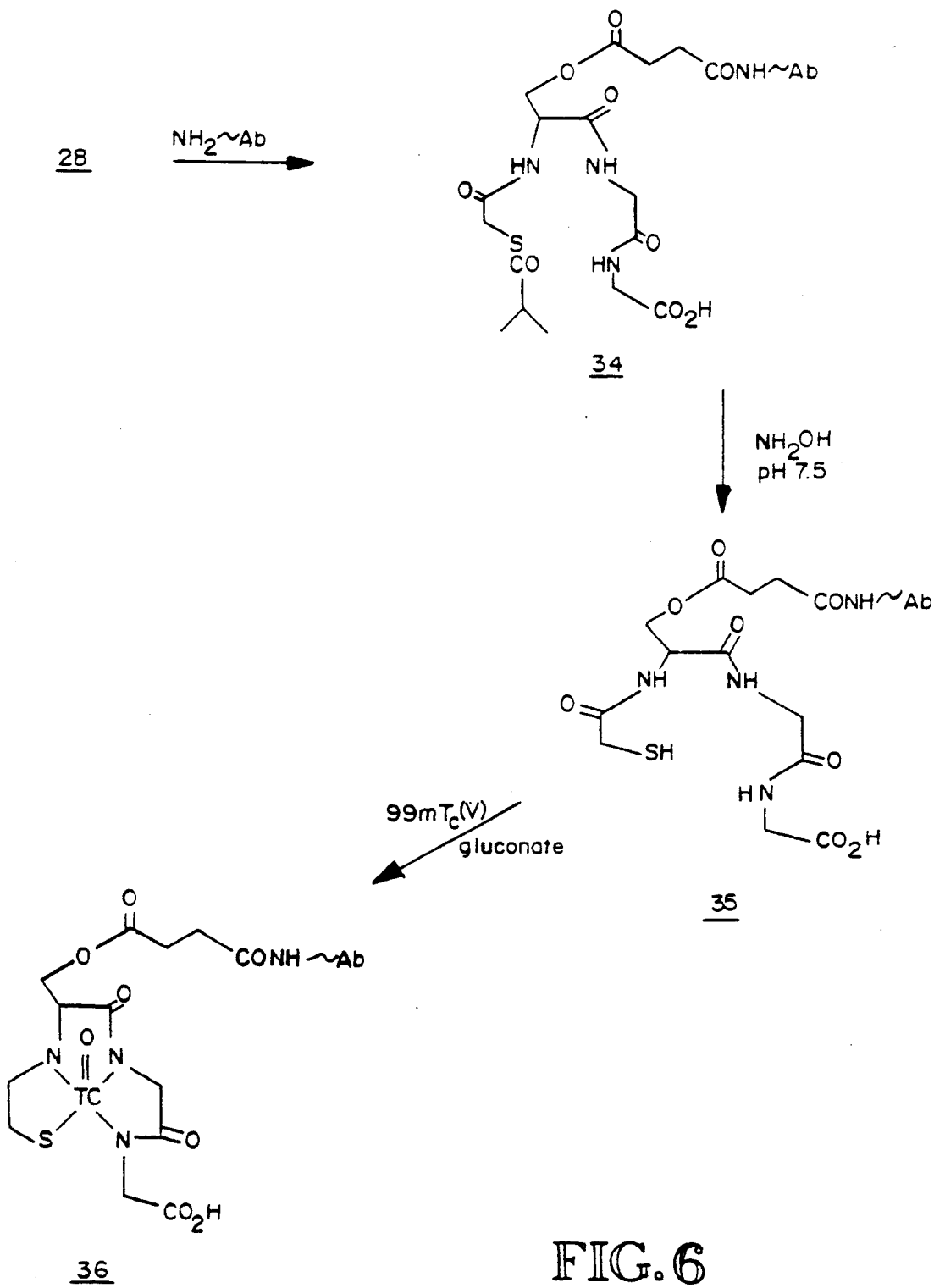

The procedure is generally as depicted in FIG. 6. To 0.5 mL (2 mg) of a 4 mg/mL solution of 34 in PBS was added 0.5 mL of degassed pH 7.6 0.1M sodium phosphate buffer containing 0.5M hydroxyl amine (prepared by dissolving 17.37 g (0.25 mol) of hydroxyl amine hydrochloride and 19.0 g (0.05 mol) of Na$_3$PO$_4$ in 400 mL of water and adjusting to pH 7.6 using 1N NaOH then diluting to 500 mL total volume). The mixture was vortexed and then gently agitated for 15 minutes before passing through a size exclusion PD-10 (Sephadex G-25n) with degassed PBS to give 2 mL of 35 as a 1 mg/mL protein fraction which was used for Tc chelation.

EXAMPLE 9

Preparation of Radiolabeled Protein 36

The procedure is generally as depicted in FIG. 6. One mL of sterile water for injection was added to a sterile vial containing a stannous gluconate complex (50 mg sodium gluconate and 1.2 mg stannous chloride dihydrate, available from Merck Frosst, Canada, in dry solid form) and the vial was gently agitated until the contents were dissolved. A sterile insulin syringe was used to inject 0.1 mL of the resulting stannous gluconate solution into an empty sterile vial. Sodium pertechnetate (0.75 mL, 15-50 mCi/mL, eluted from a $^{99}$Mo/$^{99}$Tc generator purchased from DuPont, Mediphysics, Mallinckrodt or E.R. Squibb) was added, and the vial was agitated gently to mix the contents, then incubated at room temperature for 10 minutes to form a $^{99m}$Tc-gluconate complex. To 250 μL of a 1 mg/mL solution of 35 in PBS was added 87.5 μL of pH 5.5 0.2M acetate buffer and 100 μL of the $^{99m}$Tc-gluconate complex. The mixture was placed in a 37° C. incubator for 30 minutes and the amount of radionuclide chelated to the conjugate was determined to be 78%. Purification by PD-10 column resulted in a 91% purity with 86% recovery.

EXAMPLE 10

Synthesis of Chelating Compound 47

Figure 7:
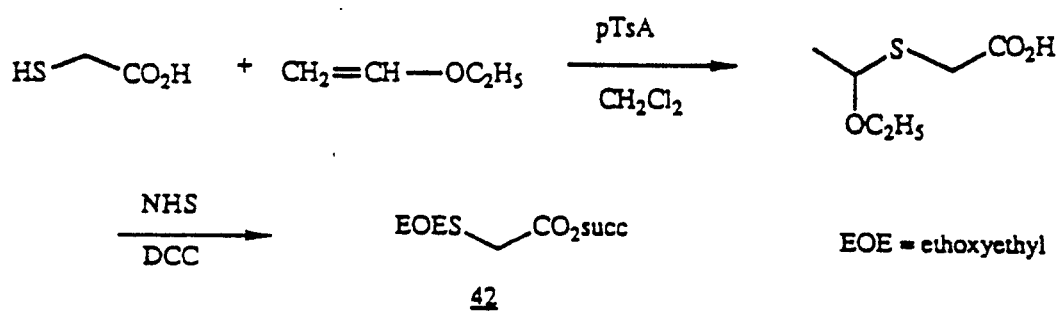
Figure 8:
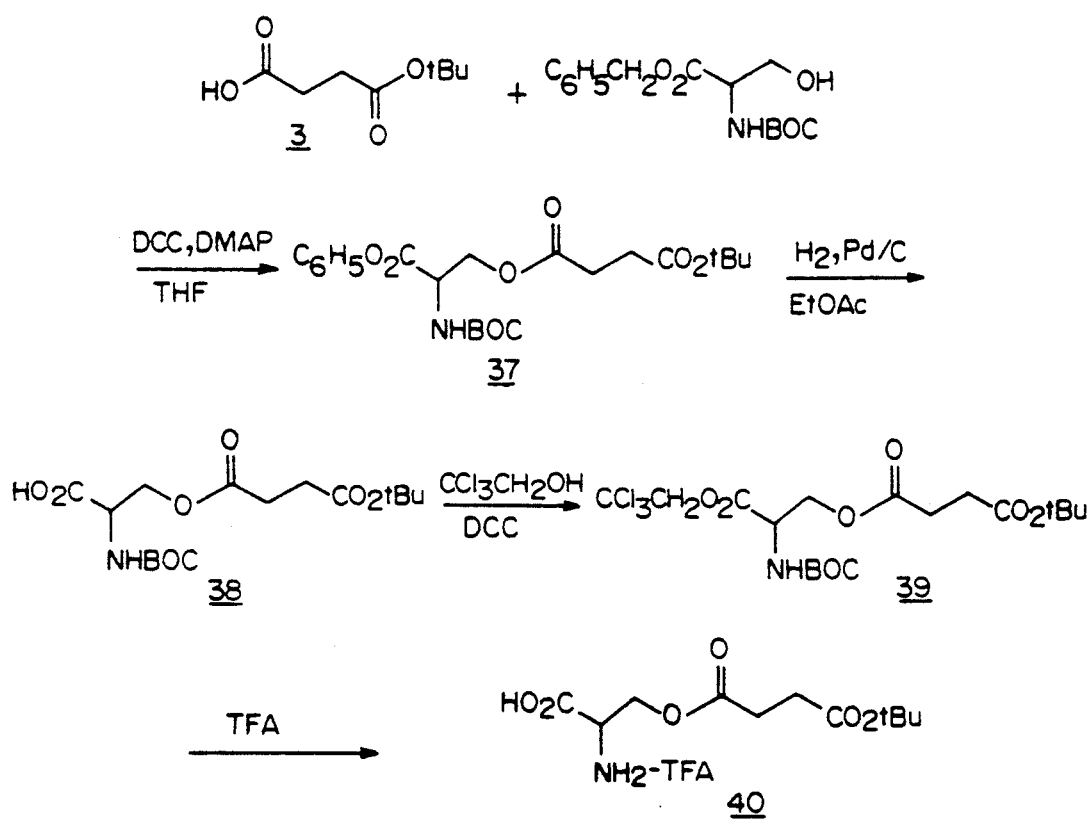
Figure 9:
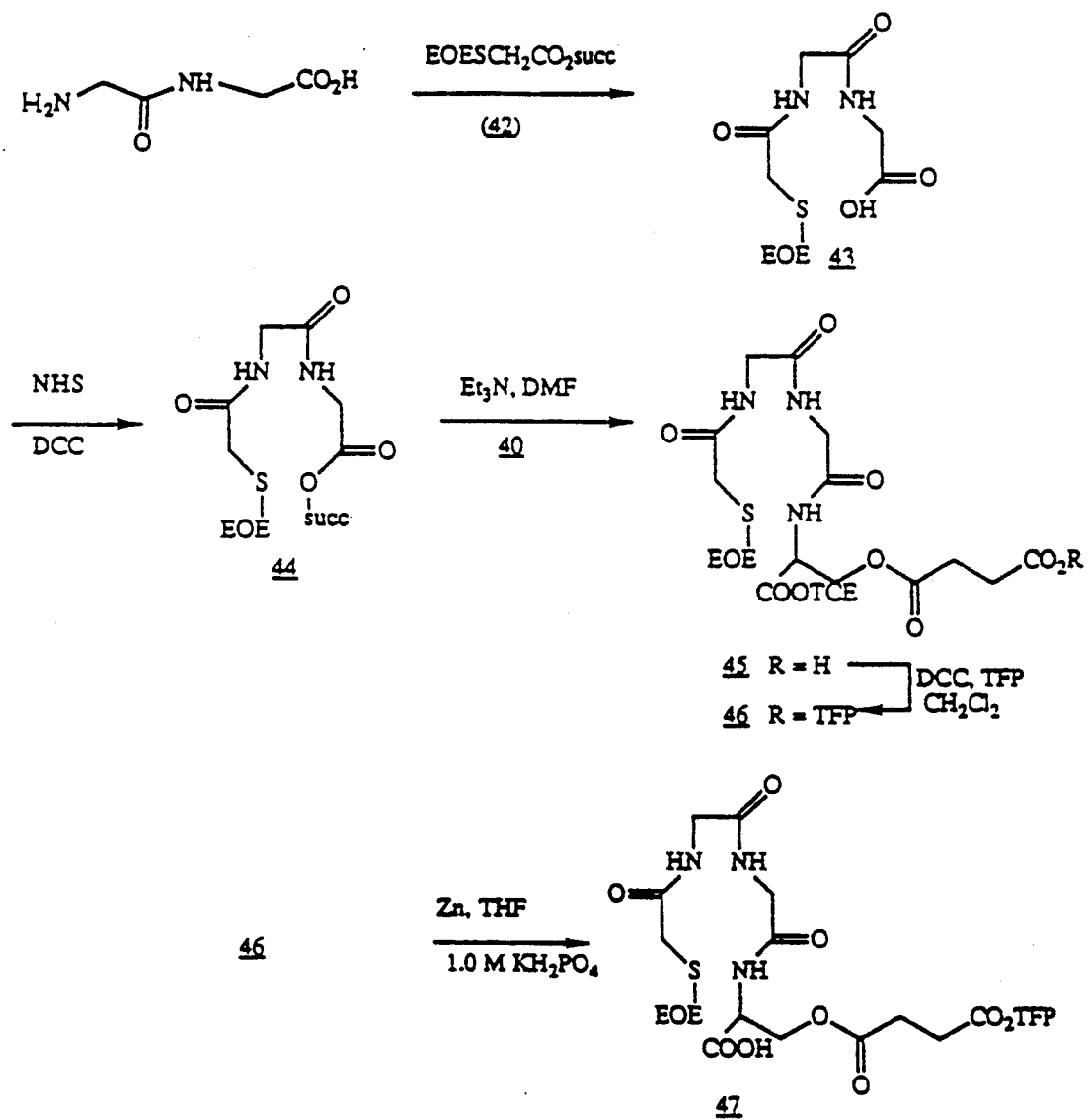

The procedure is as generally depicted in FIGS. 7-9.

Synthesis of 37

1,3-Dycyclohexylcarbodiimide (2.10 g, 10.2 mmol) was added to a stirring solution of N-tert-butoxycarbonyl-L-serine benzyl ester (from Bachem Inc.) (2.50 g, 8.5 mmol), tert-butyl hydrogen succinate prepared by the procedures of Büchi, G.; Roberts, E., *J. Org. Chem.* 1968. 33, 460 (3, 1.48 9, 8.5 mmol) and 4-dimethylaminopyridine (1.14 g, 9.3 mmol) in 17.5 mL of anhydrous THF. After stirring at room temperature for 17 hr, the mixture was filtered and evaporated in vacuo. The resulting residue was taken up in EtOAc (30 mL) and washed successively with 1N HCl (2×10 mL), H$_2$O (1×10 mL), saturated NaHCO$_3$ (2×10 mL), saturated NaCl (1×10 mL), then dried (MgSO$_4$), filtered, and evaporated. The residue was purified by flash chromatography on silica gel (30% EtOAc:hexanes). The pure 37 was isolated as a colorless oil which was used directly in the next step. $^1$H NMR (CDCl$_3$) δ 7.39 (br s, 5H), 5.45 (br d, 1H), 5.30 (m, 2H), 4.63 (m, 1H), 4.47 (m, 2H), 2.49 (br s, 4H), 1.47 (br s, 18H).

Synthesis of 38

Compound 37 isolated in the previous step was dissolved in EtOAc (20 mL) and added to 5% palladium on activated carbon (pre-moistened with EtOAc) and shaken under H$_2$ (60 psi) in a Parr apparatus at 25° C. for 20 h. The crude reaction mixture was filtered through Celite, and evaporated in vacuo. The residue was purified by flash chromatography on silica gel (50:46:4 EtOAc:hexanes:HOAc) to yield 2.92 g of 38 (95% from N-tert-butoxy-carbonyl-L-serine benzyl ester). $^1$H NMR (CDCl$_3$) δ 5.51 (br d, 1H), 4.64 (m, 1H), 4.50 (m, 2H), 2.59 (br s, 4H), 1.48 (br s, 18H).

Synthesis of 39

1,3-Dicyclohexylcarbodiimide (1.77 g, 8.57 mmol) was added to a stirring solution of 38 (2.58 g, 7.14 mmol), 2,2,2-trichloroethanol (0.69 mL, 7.14 mmol) and 4-dimethylaminopyridine (1.05 g, 8.57 mmol) in 9.0 mL of anhydrous THF. After stirring at room temperature for 16 h the mixture was filtered and evaporated in vacuo. The resulting residue was taken up in EtOAc (50 mL) and washed with 0.1 N HCl (3×30 mL), then saturated NaCl (1×20 mL), then dried (MgSO$_4$), filtered, and evaporated. The residue was purified by flash chromatography on silica gel (20% EtOAc:hexanes) to yield 1.22 g of 39 (35%). $^1$H NMR (CDCl$_3$) δ 5.48 (br d, 1H), 4.81 (m, 3H), 4.52 (m, 2H), 2.53 (br s, 4H), 1.44 (br s, 18H).

Synthesis of 40

Compound 39 (0.105 g, 0.213 mmol) was dissolved in trifluoroacetic acid (2.0 mL, 26 mmol) and stirred at room temperature for 1.5 h. The mixture was evaporated in vacuo to yield 89 mg (93%) of 40 as a colorless oil. $^1$H NMR (DMSO) δ 5.08 (m, 2H), 4.77 (m, 1H), 4.45 (d, 2H), 2.51 (m, 4H).

S-(1-ethoxyethyl)mercaptoacetic acid (5a) 41

A solution of mercaptoacetic acid (17.4 mL, 250 mmol) in 125 mL of dichloromethane containing p-toluenesulfonic acid monohydrate (0.24 g, 1.26 mmol) was cooled to −18° C. to −25° C. with stirring. Ethyl vinyl ether (23.9 mL, 250 mmol) in 125 mL of dichloromethane was added dropwise to the cold solution over a period of 90 minutes. The stirring was continued for an additional 30 minutes with the temperature maintained in the −18° C. to −25° C. range. Then 200 mL of pH=7 phosphate buffer was added, and the reaction mixture was allowed to warm with stirring for 10 to 15 minutes. The mixture was then poured into a flask containing 900 mL of ethyl acetate and 200 mL of water. Layers were separated and the aqueous portion extracted twice with ethyl acetate. The organic layers were combined, washed with brine and dried ($MgSO_4$). Removal of the solvent left 31.4 g of S-(1-ethoxyethyl)-mercaptoacetic acid 41 as a colorless oil (77% yield): $^1$H NMR ($CDCl_3$) 1.15 (t, J=7.0Hz, 3H), 1.52 (d, J=6.4Hz, 3H), 3.36 (s, 2H), 3.60 (m, 2H), 4.84 (q, J=6.4Hz, 1H), 11.65 (s, 1H). The material was used without further purification.

Succinimidyl S-(1-ethoxyethyl)mercaptoacetate 42

A solution of S-(1-ethoxyethyl)mercaptoacetic acid (5.76 g, 35.1 mmol) and N-hydroxysuccinimide (4.85 g, 42.1 mmol) was prepared in 100 mL of anhydrous THF. To this was added a solution of 1,3-dicyclohexylcarbodiimide (8.70 g, 42.1 mmol) in 65 mL of anhydrous THF. The mixture was stirred at room temperature for 2 hours or until TLC analysis indicated complete formation of the succinimidyl ester. The mixture was then filtered, and the filtrate was concentrated in vacuo to a viscous residue. The residue was dissolved in ethyl acetate, washed with water, brine, and dried ($MgSO_4$). Removal of the solvent left the crude succinimidyl ester as an oil, which was further purified by flash chromatography on silica gel, using ethyl acetate-hexanes as the column eluent, to give 5.1 g of S-(1-ethoxyethyl)-mercaptoacetic acid succinimidyl ester as a colorless oil (56% yield): $^1$H NMR ($CDCl_3$), 1.21 (t, J=7.0Hz, 3H), 1.58 (d, J=6.4Hz, 3H), 2.83 (s, 4H), 3.60 (m, 4H), 4.88 (q, J=6.4Hz, 1H).

Synthesis of 43

Solid $NaHCO_3$ (1.09 g, 13.0 mmol) was added to a solution of glycylglycine (1.22 g, 9.3 mmol) in 10 mL of water. After gas evolution ceased, a solution of 42 (2.66 g, 10.2 mmol) in 12 mL of $CH_3CN$ was added to the reaction mixture. The mixture was stirred at room temperature for 22 h, then evaporated in vacuo. The residue was purified by flash chromatography on silica gel (85:10:5 $CH_3CN:H_2O:HOAc$) to yield 2.2 g (86%) of 43 as a viscous oil. $^1$H NMR (DMSO) 8.26 (t, 1H), 8.08 (t, 1H), 4.80 (q, 1H), 3.73 (m, 4H), 3.52 (m, 2H), 3.24 (s, 2H), 1.43 (d, 3H), 1.10 (t, 3H).

Synthesis of 44

1,3-Dicyclohexylcarbodiimide (0.66 g, 3.2 mmol) was added to a stirring solution of 43 (0.81 g, 2.9 mmol) and N-hydroxysuccinimide (0.37 g, 3.2 mmol) in 10 mL of $CH_3CN$. After stirring for 2 h, the mixture was filtered and the filtrate was evaporated in vacuo. The residue was purified by flash chromatography on silica gel (96:4 EtOAc:HOAc) to yield 0.80 g (73%) of 44 as a viscous oil. $^1$H NMR (DMSO) δ 8.54 (t, 1H), 8.29 (t, 1H), 4.80 (q, 1H), 4.27 (d, 2H), 3.78 (d, 2H), 3.53 (m, 2H), 3.24 (s, 2H), 2.81 (s, 4H), 1.43 (d, 3H), 1.09 (t, 3H).

Synthesis of 45

Triethylamine (0.039 mL, 0.28 mmol) was added to a solution of 40 (83 mgs, 0.18 mmol) and 44 (104 mgs, 0.28 mmol) in 1.0 mL of anhydrous DMF. After stirring at room temperature for 2.5 h the mixture was evaporated in vacuo. The resulting residue was taken up in EtOAc (20 mL) and washed with water (5×10 mL), saturated NaCl (1×10 mL), then dried ($Na_2SO_4$), filtered, and evaporated. The residue was purified by flash chromatography on Baker C-18 gel (J.T. Baker $C_{18}$ gel #7025) (50:47:3 $CH_3CN:H_2O:HOAc$) to yield 68 mg (62%) of 45 as an oil. $^1$H NMR (DMSO) δ 8.58 (d, 1H), 8.29 (t, 1H), 8.20 (t, 1H), 4.93 (m, 2H), 4.79 (m, 2H), 4.33 (m, 2H), 3.82 (d, 2H), 3.73 (d, 2H), 3.52 (m, 2H), 3.22 (s, 2H), 2.49 (m, 4H), 1.43 (d, 3H), 1.09 (t, 3H).

Synthesis of 46

1,3-Dicyclohexylcarbodiimide (37 mg, 0.18 mmol) was added to a stirring solution of 45 (64 mg, 0.11 mmol) and 2,3,5,6-tetrafluorophenol (46 mg, 0.28 mmol) in $CH_2Cl_2$ (0.8 mL). After stirring at room temperature for 4.5 h, the mixture was filtered and evaporated in vacuo. The residue was purified by flash chromatography on silica gel (96:4 EtOAc:HOAc) to yield 64 mgs (80%) of 46 as a viscous oil. $^1$H NMR (DMSO) δ 8.59 (d, 1H), 8.24 (t, 1H), 8.17 (t, 1H), 7.94 (m, 1H), 4.92 (m, 2H), 4.81 (m, 2H), 4.36 (m, 2H), 3.80 (d, 2H), 3.73 (d, 2H), 3.53 (m, 2H), 3.22 (s, 2H), 3.04 (m, 2H), 2.76 (m, 2H), 1.42 (d, 3H), 1.08 (t, 3H).

Synthesis of 47

Zinc dust (124 mg, 1.9 mmol) was added in portions to a stirring solution of 46 (57 mg, 0.076 mmol) and 1.0 M $KH_2PO_4$ (0.25 mL) in 0.6 mL of THF. After stirring at room temperature for 1.5 h the mixture was filtered through celite and evaporated in vacuo. The residue was purified by flash chromatography on Baker C-18 gel (50:47:3 $CH_3CN:H_2O:HOAc$), followed by preparative C-18 HPLC (50:49:1 $CH_3CN:H_2O:HOAc$) to yield 16 mg (34%) of pure 47 as a white solid. $^1$H NMR (DMSO) δ 8.30 (d, 1H), 8.26 (t, 1H), 8.17 (t, 1H), 7.96 (m, 1H), 4.81 (q, 1H), 4.59 (m, 1H), 4.30 (m, 2H), 3.76 (m, 4H), 3.52 (m, 2H), 3.24 (s, 2H), 3.07 (m, 2H), 2.74 (m, 2H), 1.43 (d, 3H), 1.10 (t, 3H).

Chelating compound 47 was radiolabeled and attached to a targeting protein using the same procedures described in example 4.

EXAMPLE 11

Alternative Route to Compound 9, an Intermediate in the Synthesis of Chelating Compound 13

Figure 10:
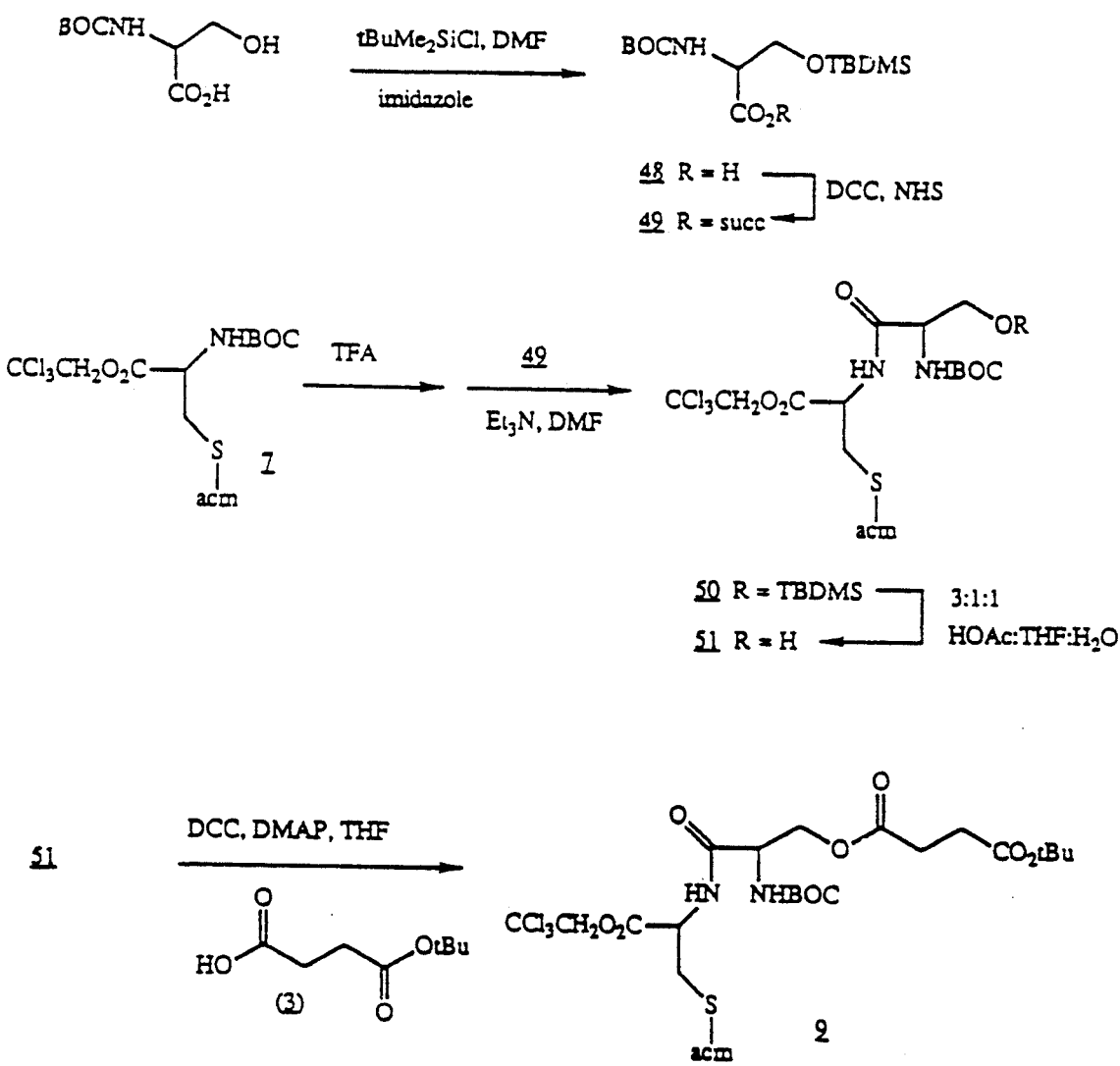

The synthesis procedure is generally as depicted in FIG. 10.

Synthesis of N-t-BOC-serine-O-t-butyldimethylsilyl ether 48. (LG762-21)

To a solution of N-BOC-serine (615 mg, 3.00 mmol) and imidazole (449 mg, 6.60 mmol) in DMF (10.0 mL), was added t-butyldimethylsilyl chloride (994 mg, 6.60 mmol). The reaction solution was stirred at room temperature for 15 hours and then concentrated. The residue was dissolved in EtOAc (50 mL) and washed with water (25 mL), brine (25 mL), and dried to give 48 as a white foam (1.00 g, 3.0 mmol, theoretical yield). $^1$H NMR (DMSO): 0.05 (s, 4H), 0.90 (s, 9H), 1.40 (s, 9H), 3.80 (t, 2H), 4.10 (m, 1H), 6.75 (m, 1H).

Synthesis of N-t-BOC-serine-O-t-butyldimethylsilylsuccinimidyl ester 49. (LG762-22)

To an ice cold solution of 48 (1.00 g, 3.0 mmol) in acetonitrile (4.5 mL) was added NHS (414 mg, 3.60 mmol) followed by DCC (712 mg, 3.45 mmol). The solution was warmed to room temperature and stirred for 16 hours. The mixture was treated with acetic acid (0.10 mL), cooled to 0°, and filtered. The filtrate was evaporated to give 49 as a white foam (1.25 g, 3.0 mmol, theoretical yield). $^1$H NMR (DMSO): 0.05 (s, 4H), 0.90 (s, 9H), 1.40 (s, 9H), 3.80 (s, 4H), 3.90 (m, 2H), 4.50 (m, 1H), 7.45 (d, 1H).

Synthesis of 50. (LG762-32)

To a solution of 7 (1.02 g, 2.41 mmol) in $CH_2Cl_2$ (5.6 mL) was added trifluoroacetic acid (5.6 mL). The solution was stirred at room temperature for 1 hour and then coevaporated with $CCl_4$ (3×30 mL). The residue (8) was dissolved in DMF. To this solution at 0° was added a solution of 49 (1.00 g, 2.41 mmol) in DMF (5.0 mL). To this was added triethylamine (0.84 mL, 6.02 mmol). The reaction solution was stirred at room temperature for 16 hours. Additional triethylamine (0.20 mL) was added and the reaction was stirred for 1 hour. The solution was concentrated. The residue was dissolved in EtOAc (40 mL) and washed with pH 4.0 buffer. The aqueous was washed with EtOAc (30 mL). The combined EtOAc extracts were washed with brine, dried, and evaporated to give an oil. The oil was chromatographed (1:1 EtOAc:Hexanes 1% HOAc) to give 50 as a white foam (0.89 g, 1.52 mmol, 63%). $^1$H NMR (DMSO): 0.05 (s, 5H), 0.80 (s, 9H), 1.35 (s, 9H), 1.85 (s, 3H), 2.95 (ddd, 2H), 3.70 (m, 2H), 4.20 (m, 3H), 4.60 (m, 1H), 4.85 (dd, 2H), 6.65 (broad d, 1H), 8.55 (m, 2H).

Synthesis of 51. (LG762-28)

A solution of 50 (200 mg, 0.34 mmol) in 3:1:1 HOAc:H$_2$O:THF (1.3 mL) was stirred at room temperature for 60 hours. The solution was partitioned between EtOAc and water. The aqueous was extracted with EtOAc (2×20 mL). The combined EtOAc extracts were washed with brine, dried, and evaporated to give 51 as an oil (175 mg, 0.34 mmol, theoretical yield). $^1$H NMR (CDCl$_3$): 1.40 (s, 9H), 1.95 (s, 3H), 3.05 (ddd, 2H), 3.65 (dd, 1H), 4.05 (dd, 1H), 4.15–4.50 (m, 3H), 4.70 (dd, 2H), 4.90 (m, 1H), 5.75 (m, 1H), 6.70 (m, 1H), 7.75 (m, 1H).

Synthesis of 52. (LG762-30)

To an ice cold solution of 51 (90 mg, 0.18 mmol), 3 (31 mg, 0.18 mmol), and DMAP (24 mg, 0.19 mmol) in THF (0.6 mL), was added DCC (43 mg, 0.21 mmol). The solution was warmed to room temperature and stirred for 18 hours. The mixture was filtered and rinsed with cold acetonitrile. The filtrate was evaporated. The residue was chromatographed (50% EtOAc:Hexanes 1% HOAc, 300 mL, then 75% EtOAc:Hexanes 1% HOAc, 300 mL) to give 52 as an oil (60 mg, 0.09 mmol, 51%). $^1$H NMR (CDCl$_3$): 1.50 (s, 18H), 2.05 (s, 3H), 2.60 (broad s, 4H), 3.10 (m, 2H), 4.35–4.60 (m, 5H), 4.60–5.05 (overlapping dd and s, 3H), 5.70 (m, 1H), 6.75 (broad s, 1H), 7.70 (broad d, 1H).

EXAMPLE 12

Analysis of Stereochemical Isomers of $^{99m}$Tc-Labeled Chelates

Analyses of the technetium labeled N$_3$S and N$_2$S$_2$ chelates were performed by isocratic reverse phase C$_{18}$ HPLC in 24% acetonitrile mobile phase at a flow rate of 1 mL/min. Compound 20 afforded two epimeric technetium complexes A and B in the ratio of 1:7. Radiometric peaks A and B refer to the order of elution off HPLC. Compound 47 on the other hand afforded two diastereometric technetium complexes (Peaks A and B) in the ratio of 1:1. Compound 13 upon technetium complexation resulted in a mixture of epimeric peaks A and B in the ratio of 1:8.

EXAMPLE 13

Biodistribution Studies

Biodistribution of $^{99m}$Tc-labeled antibody fragments prepared above was analyzed in a rat model. The antibody fragments were labeled with $^{99m}$Tc chelates prepared from compounds 13, 20, or 47. (See examples 4 and 10.)

The three studies were conducted in male Sprague Dawley rats weighing about 200–300 grams. The rats were received and acclimated to the facility 5 to 7 days prior to use in a study. Four rats were used for each timepoint in each study.

The rats were placed under a heat lamp to dilate their tail veins. 100 ug of one of the radiolabeled antibody fragments (in a volume of 200–300 uL) was injected into each rat intravenously via the tail vein. Depending on the specific activity of the individual preparation of radiolabeled antibody fragment, the amount of radioactivity injected was between 200 uCi and 1 mCi. Biodistribution was analyzed at each of four timepoints (3 hours, 6 hours, 10 hours, and 20 hours post-injection.) At each timepoint, four rats were anesthetized with halothane (inhalant) until they showed no reflexive responses. Three mL of blood was then collected, followed by sacrifice of the rats using euthanasia solution. Both procedures were done via cardiac puncture.

Each rat was dissected and the following tissues were collected, weighed, and placed in tubes for counting using a gamma counter. The results of the three studies are presented in FIGS. 11-13, where the percentage of the total injected dose of radioactivity that had localized in each of the tissues (the entire organ) is shown. In the figures, BL represents blood, LV represents liver, ST represents stomach, KD represents kidneys, and INT represents intestines. For each conjugate, Ab represents the monoclonal antibody fragment.

The top graph in each figure presents biodistribution data for the same antibody fragment labeled with the $^{99m}$Tc-N$_3$S chelate shown. This conjugate does not have a linkage comprising a cleavable ester, and is presented for comparative purposes.

EXAMPLE 14

Biodistribution Studies for Conjugates Comprising Esters in the Opposite Orientation Biodistribution studies were conducted using the procedures of example 13 for the following conjugates, in which Ab represents a Fab fragment of monoclonal antibody NR-LU-10:

purity: 94%
specific activity: 5.08 mCi/mg
dose: 100 micrograms

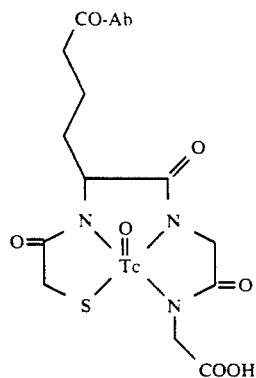

purity: 95%
specific activity: 2.94 mCi/mg
dose: 100 micrograms

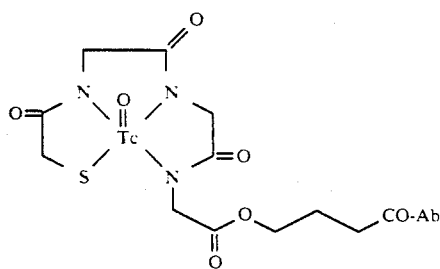

The first chelate is the same one used for comparative purposes in example 13. There is no ester in the linkage between the chelate core and the antibody fragment in the conjugates comprising this chelate. The second chelate comprises an ester in the linkage to the antibody fragment, but the ester has an orientation opposite to that of the compounds of the present invention.

The results are presented in FIG. 14. Localization of radioactivity within the intestines was relatively high for the second conjugate. Thus, the presence of an ester per se in the linkage was not sufficient to reduce intestinal radioactivity levels over those of the first conjugate. While not wishing to be bound by theory, the particular ester-containing linkage in the second conjugate may not be readily cleavable under physiological conditions. The free acid form of the chelate that would be released by ester cleavage was not detected by HPLC. The relatively high intestinal radioactivity levels may be attributable to hepatobiliary excretion of the lysine adduct of the chelate, which would be expected to be a major catabolite if the ester is not efficiently cleaved.

Another biodistribution study was conducted by the same procedures for the following conjugates, in which Ab represents the NR-LU-10 Fab antibody fragment:

Conjugate "A"
purity: 92%
specific activity: 6.30 mCi/mg
dose: 100 micrograms

-continued

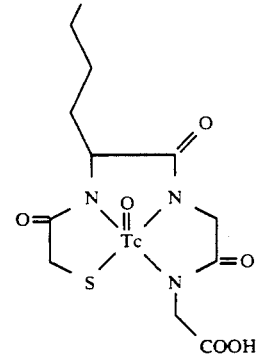

Conjugate "C"
purity: 91%
specific activity: 3.90 mCi/mg
dose: 100 micrograms

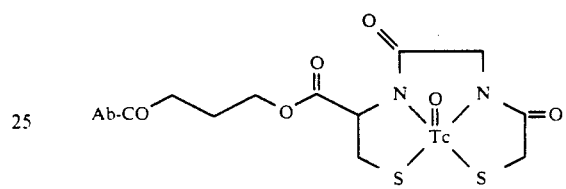

The results are presented in FIG. 15. As before, the presence of an ester (in the orientation opposite to that of the esters in conjugates of the present invention) in the linkage to the antibody fragment was not sufficient to promote enhanced biodistribution properties. Specifically, intestinal radioactivity levels were relatively high for the ester-containing conjugate "C".

EXAMPLE 15

Synthesis of Chelating Compound 58

Figure 16:
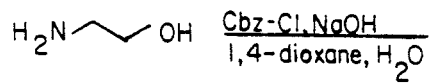
Figure 16:
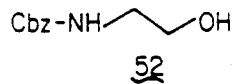
Figure 16:
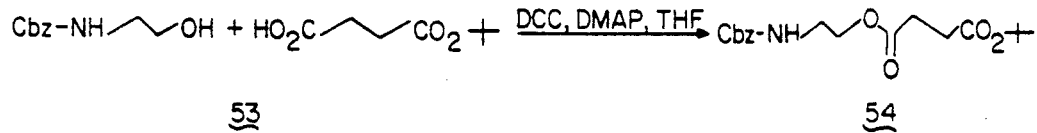
Figure 16:
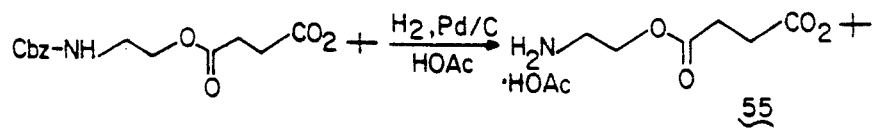
Figure 16:
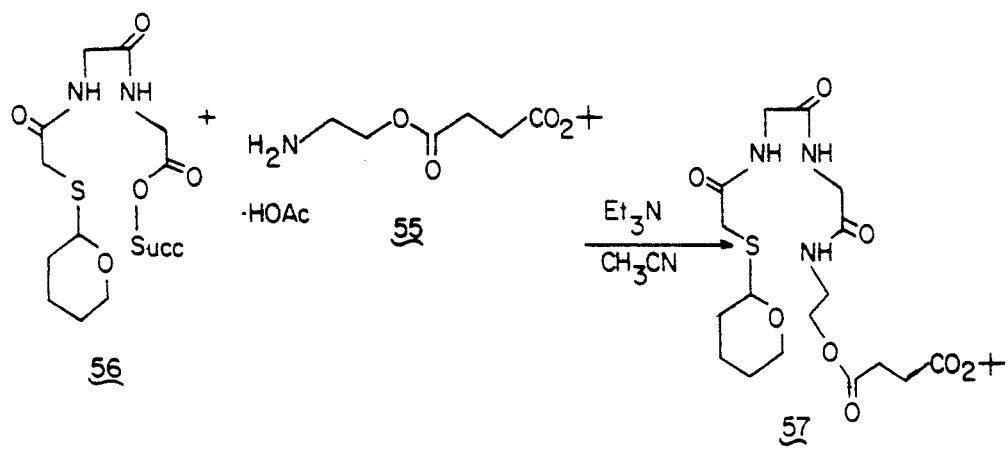
Figure 16:
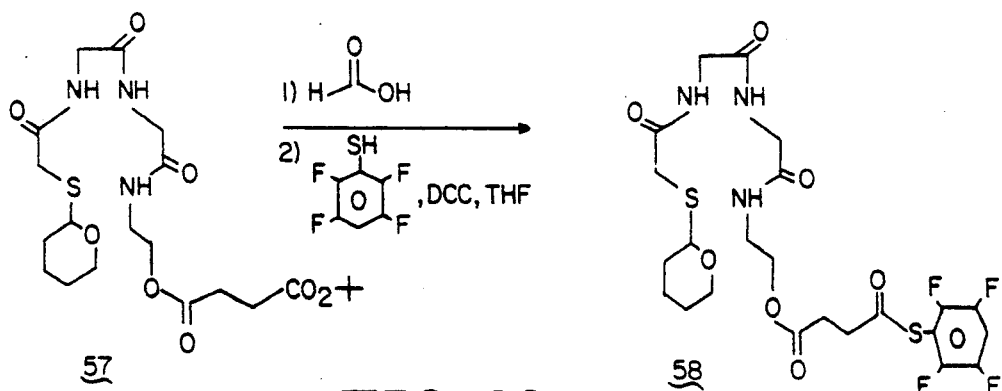

The procedure is generally as depicted in FIG. 16. Dissolve 6.1 g (10 mmol) of ethanolamine in 10 mL of 1N NaOH. Cool the solution with an ice bath and add to it a solution of 1.7 g (10 mmol) of benzyl chloroformate dissolved in 10 mL of 1,4-dioxane, dropwise, over a period of 30 minutes. When the addition is complete, remove the ice bath and stir for 30 minutes. Add 100 mL of ethyl acetate and wash with 3×50 mL of 1.0N HCl. Wash the ethyl acetate layer with 50 mL of brine. Dry the ethyl acetate layer over anhydrous sodium sulfate. Filter and concentrate the filtrate to a residue. Final purification is achieved by flash chromatography on silica gel with ethyl acetate/hexane as the eluent. N-Cbz-ethanolamine, compound 52, is isolated as an oil.

Dissolve 0.87 g (5.0 mmol) of tert-butyl hydrogen succinate, compound 53, [prepared by the procedure of Büchi and Roberts, J. Org. Chem., 33 460 (1968)], and 0.98 g. (5.0 mmol) of N-Cbz-ethanolamine, compound 52, in 8.0 mL of anhydrous tetrahydrofuran. Add 0.67 g (5.5 mmol) of 4-dimethylaminopyridine and cool the mixture with an ice bath. Add 1.13 g (5.5 mmol) of 1,3-dicyclohexylcarbodiimide, followed by 2.0 mL of anhydrous tetrahydrofuran. Stir for 10 minutes then remove the ice bath and continue stirring for 24 hours. Filter the reaction mixture and concentrate the filtrate to a residue. Dissolve the residue in 50 mL of ethyl acetate and wash it with 2×25 mL of 1.0N HCl, then wash it with 25 mL of brine. Dry the ethyl acetate layer over anhydrous sodium sulfate. Filter and concentrate the filtrate to a residue. Final purification is achieved by flash chromatography on silica gel with ethyl acetate/hexane as the eluent. The product, compound 54 is isolated as an oil.

Add 1.05 g (3.0 mmol) of compound 54 to a Parr bottle containing 0.1 g of 5% Palladium on activated carbon and 10 mL of acetic acid. Shake under 60 psi hydrogen for 24 hours. Filter through celite and concentrate the filtrate to give compound 55, as the acetic acid salt.

Dissolve 0.39 g (1.0 mmol) of S-THP-mercaptoacetylglycylglycine succinimidyl ester, compound 56, (prepared as described in U.S. Patent No. 4,897,255) and 0.28 g (1.0 mmol) of compound 55, in 10 mL of acetonitrile. Add 0.11 g (1.1 mmol) of triethylamine and stir at room temperature for 3 hours. Concentrate the mixture to a residue. Dissolve the residue in 60 mL of ethyl acetate and wash with 2×40 mL of 0.1N HCl, then 40 mL of saturated aqueous sodium bicarbonate, then 40 mL of brine. Dry the ethyl acetate layer over anhydrous sodium sulfate. Filter and concentrate the filtrate to a residue. Dry the residue in vacuo to give the product, compound 57, as a white solid in 52% yield.

Dissolve 0.114 g (0.233 mmol) of compound 57 in 3.0 mL of 96% formic acid. Stir the reaction mixture for 3 hours at room temperature. Remove the formic acid in vacuo to give a residue. Dissolve the residue in 2.0 mL of anhydrous tetrahydrofuran. Add 0.127 g (0.697 mmol) of 2,3,5,6-tetrafluorothiophenol, followed by 0.144 g (0.697 mmol) of 1,3-dicyclohexylcarbodiimide. Stir the reaction mixture at room temperature for 24 hours. Concentrate the reaction mixture to a residue. Final purification of compound 58 is achieved by preparative HPLC, to give a 50% yield of purified compound 58.

EXAMPLE 16

Preparation of Radiolabeled Protein

To a lyophilized vial containing stannous gluconate (100 μg stannous chloride and 2.5 mg sodium gluconate with 100 μg gentisic acid as a stabilizer and 40 mg lactose as a diluent), pH 1.8, 1.0 mL of sodium pertechnetate (5–100 mCi) was added. Immediately following, 100 μg of chelating compound 58 dissolved in 400 μl of isopropanol was added. The reaction mixture was mixed thoroughly and incubated at 100° C. for 10 minutes to effect transfer of $^{99m}Tc$ into the chelate. The reaction mixture was then cooled to room temperature. The typical radio-chemical yield of $^{99m}Tc$-labeled ester-containing chelate is ~80% analyzed by HPLC.

The $^{99m}Tc$ radionuclide metal chelate was then attached to an antibody. 2.0 mL of 250 mM carbonate buffer, pH 9.3, was added to the reaction mixture followed immediately by 0.5 mL of 10 mg/mL whole antibody or fragment thereof (e.g., Fab fragment) in phosphate buffered saline. The reaction mixture was allowed to conjugate at room temperature for 20 minutes. The reaction mixture was then purified via size exclusion chromatography or anion exchange chromatography. Overall radio-chemical yield of the $^{99m}Tc$ radiolabeled chelate-antibody conjugate was ~40% with a final purity of 85–90%.

What is claimed is:

1. A compound of the formula:

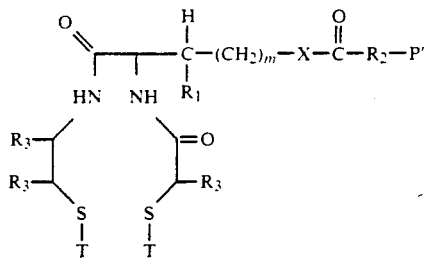

wherein:

m is 0 or 1;

$R_1$ represents H or $CH_3$;

X represents O or S;

each $R_3$ is independently selected from H, $CH_2OH$, $CH_3$, $-(CH_2)_n-CONH_2$, and $-(CH_2)_n-COOH$, wherein n is 0 to about 2, with at least one $R_3$ substituent being $-(CH_2)_n-COOH$;

T' and T each represent hydrogen or a sulfur protecting group;

$R_2$ represents a spacer; and

P' represents a targeting molecule or a conjugation group.

2. The compound of claim 1, wherein $R_2$ is selected from: $-(CH_2)_{n'}-$, wherein n' is 2–5;

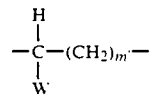

wherein W represents an electron withdrawing or electron donating group and m' is 1–4;

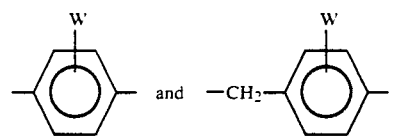

wherein W represents an optional electron withdrawing or electron donating group.

3. The compound of claim 2 wherein X is O and $R_2$ is $-(CH_2)_2-$.

4. A compound of the formula:

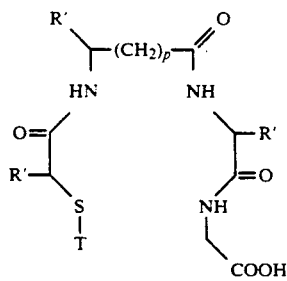

wherein p is 0 or 1;

one of the R' symbols represents

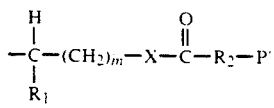

and the others are selected from H, CH$_3$, CH$_2$OH, —(CH$_2$)$_n$—CONH$_2$ and (CH$_2$)$_n$—COOH wherein n is 0 to about 2;

m is 0 or 1;

R$_1$ represents H or CH$_3$;

X represents O or S;

T represents hydrogen or a sulfur protecting group;

R$_2$ represents a spacer; and

P' represents a targeting molecule or a conjugation group.

5. The compound of claim 4, wherein R$_2$ is selected from: —(CH$_2$)$_{n'}$—, wherein n' is 2-5;

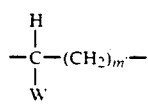

wherein W represents an electron donating or electron withdrawing group and m' is 1-4;

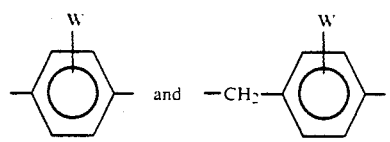

wherein W represents an optional electron donating or electron withdrawing group.

6. The compound of claim 4, wherein p is 0, X is O and R$_2$ is —(CH$_2$)$_2$—.

7. A compound of the formula:

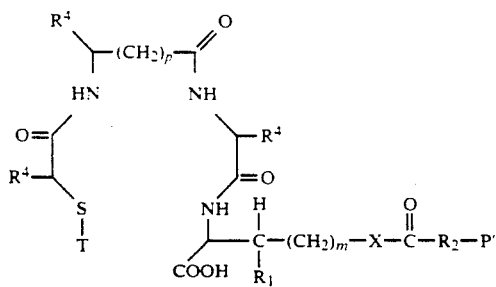

wherein p is 0 or 1;

each R$^4$ is independently selected from H, CH$_3$, CH$_2$OH, —(CH$_2$)$_n$—CONH$_2$ and —(CH$_2$)$_n$—COOH wherein n is 0 to about 2;

m is 0 or 1;

R$_1$ represents H or CH$_3$;

X represents O or S;

T represents hydrogen or a sulfur protecting group;

R$_2$ represents a spacer; and

P' represents a targeting molecule or a conjugation group.

8. The compound of claim 7, wherein R$_2$ is selected from: —(CH$_2$)$_{n'}$—, wherein n' is 2-5;

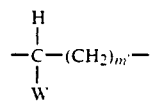

wherein W represents an electron donating or electron withdrawing group and m' is 1-4;

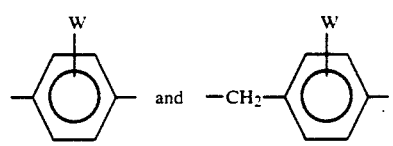

wherein W represents an optional electron donating or electron withdrawing group.

9. The compound of claim 7 wherein each R$_4$ is H, p is 0, X is O and R$_2$ is —(CH$_2$)$_2$—.

10. A compound of the formula:

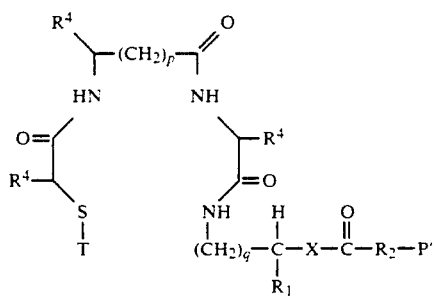

wherein p is 0 or 1;

each R$^4$ is independently selected from H, CH$_3$, CH$_2$OH, —(CH$_2$)$_n$—CONH$_2$ and (CH$_2$)$_n$—COOH wherein n is 0 to about 2;

q is 1, 2, or 3;

R$_1$ represent H or CH$_3$;

X represents O or S;

T represents hydrogen or a sulfur protecting group;

R$_2$ represents a spacer; and

P' represents a targeting molecule or a conjugation group.

11. The compound of claim 10 wherein R$_2$ is selected from: —(CH$_2$)$_{n'}$—, wherein n' is 2-5;

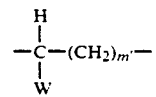

wherein W represents an electron donating or electron withdrawing group and m' is 1-4;

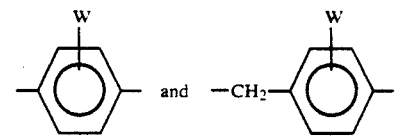

wherein W represents an optional electron donating or electron withdrawing group.

12. The compound of claim 10 wherein p is 0, X is O, R$_2$ is —(CH$_2$)$_2$—, one R$^4$ symbol represents —(CH$_2$-

)$_n$—COOH wherein n is 0 to about 2, and the other R$^4$ symbols represent H.

13. A compound of the formula:

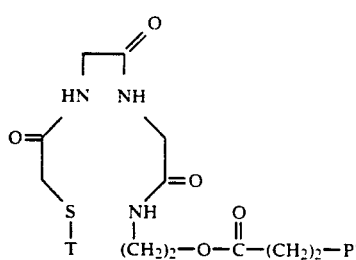

wherein T represents hydrogen or a sulfur protecting group and P' represents a targeting molecule or a conjugation group.

14. The compound of claim 13 wherein T represents a hemithioacetal sulfur protecting group and P' represents an active ester.

15. The compound of claim 1, 4, 7, or 10 wherein the conjugation group is selected from the group consisting of active esters, isothiocyanates, amines, hydrazines, thiols, maleimides or other Michael acceptors, and activated halides.

16. The compound of claim 15 wherein the conjugation group is an active ester.

17. The compound of claim 1, 4, 7 or 10 wherein the targeting molecule is a monoclonal antibody or an antigen binding fragment thereof.

18. A compound of the formula:

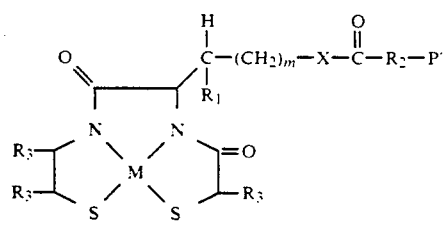

and stereochemical isomers thereof, wherein:

M represents a radionuclide metal or oxide thereof;
m is 0 or 1;
R$_1$ represents H or CH$_3$;
X represents O or S;
each R$_3$ is independently selected from H, CH$_3$, CH$_2$OH, —(CH$_2$)$_n$—CONH$_2$, and —(CH$_2$)$_n$—COOH, wherein n is 0 to about 2, with at least one R$_3$ substituent being —(CH$_2$)$_n$—COOH;
R$_2$ represents a spacer; and
P' represents a targeting molecule or a conjugation group.

19. The compound of claim 18, wherein R$_2$ is selected from: —(CH$_2$)$_{n'}$—, wherein n' is 2-5;

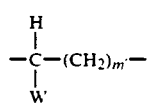

wherein W represents an electron donating or electron withdrawing group and m' is 1-4;

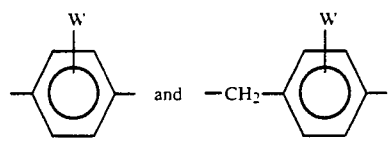

wherein W represents an optional electron donating or electron withdrawing group.

20. The compound of claim 18 wherein X is O, and R$_2$ is —(CH$_2$)$_2$—.

21. A compound of the formula:

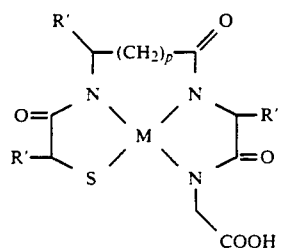

and stereochemical isomers thereof, wherein
M represents a radionuclide metal or oxide thereof;
p is 0 or 1;
one of the R' symbols represents

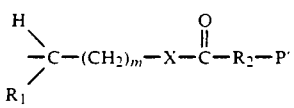

and the others are selected from H, CH$_3$, CH$_2$OH, (CH$_2$)$_n$—CONH$_2$ and (CH$_2$)$_n$—COOH wherein n is 0 to about 2;
m is 0 or 1;
R$_1$ represents H or CH$_3$;
X represents O or S;
T represents hydrogen or a sulfur protecting group;
R$_2$ represents a spacer; and
P' represents a targeting molecule or a conjugation group.

22. The compound of claim 21, wherein R$_2$ is selected from: —(CH$_2$)$_{n'}$—, wherein n' is 2-5;

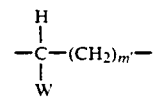

wherein W represents an electron donating or electron withdrawing group and m' is 1-4;

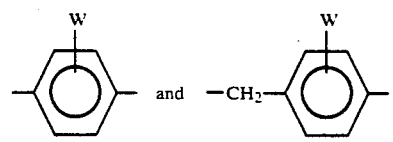

wherein W represents an optional electron donating or withdrawing group.

23. The compound of claim 21 wherein p is 0, X is O, and R$_2$ is —(CH$_2$)$_2$—.

24. A compound of the formula:

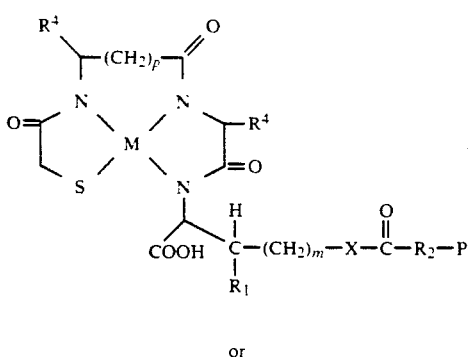

or

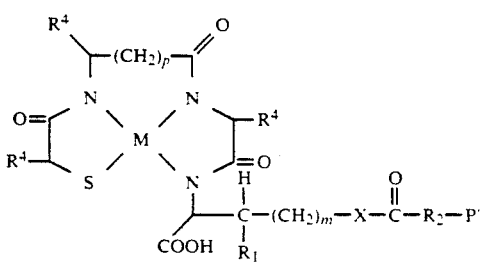

and stereochemical isomers thereof, wherein

M represents a radionuclide metal or oxide thereof;

p is 0 or 1;

each $R_4$ is independently selected from H, $CH_3$, $CH_2OH$, $-(CH_2)_n-CONH_2$ and $-(CH_2)_n-COOH$ wherein n is 0 to about 2;

m is 0 or 1;

$R_1$ represents H or $CH_3$;

X represents O or S;

$R_2$ represents a spacer; and

P' represents a targeting molecule or a conjugation group.

25. The compound of claim 24, wherein $R_2$ is selected from: $-(CH_2)_{n'}-$, wherein n' is 2-5;

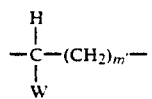

wherein W represents an electron donating or electron withdrawing group and m' is 1-4;

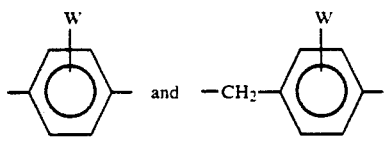

wherein W represents an optional electron donating or withdrawing group.

26. A compound of the formula:

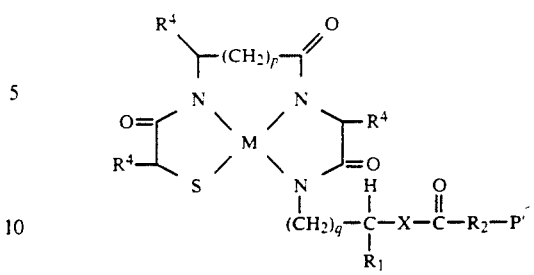

and stereochemical isomers thereof, wherein

M represents a radionuclide metal or oxide thereof;

p is 0 or 1;

each $R_4$ is independently selected from H, $CH_3$, $CH_2OH$, $-(CH_2)_n-CONH_2$ and $-(CH_2)_n-COOH$ wherein n is 0 to about 2;

q is 1, 2, or 3;

$R_1$ represents H or $CH_3$;

X represents O or S;

T represents hydrogen or a sulfur protecting group;

$R_2$ represents a spacer; and

P' represents a targeting molecule or a conjugation group.

27. The compound of claim 26 wherein $R_2$ is selected from: $-(CH_2)_{n'}-$, wherein n' is 2-5;

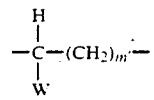

wherein W represents an electron donating or electron withdrawing group and m' is 1-4;

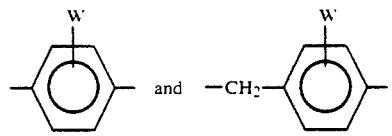

wherein W represents an optional electron donating or electron withdrawing group.

28. The compound of claim 26 wherein p is 0, X is O, $R_2$ is $-(CH_2)_2$, one $R_4$ symbol represents $-(CH_2)_n-COOH$, wherein n is 0 to about 2, and the other $R_4$ symbols represent H.

29. A compound of the formula:

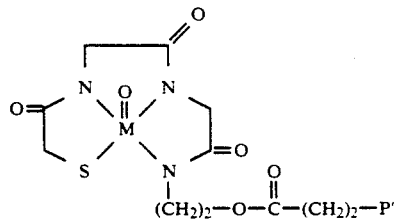

and stereochemical isomers thereof, wherein M represents a radionuclide metal selected from $^{99m}Tc$, $^{188}Re$, and $^{186}Re$, and P' represents a targeting molecule or a conjugation group.

30. The compound of claim 18, 21, 24, or 26 wherein the conjugation group is selected from the group consisting of active esters, isothiocyanates, amines, hydrazines, thiols, maleimides or other Michael acceptors, and activated halides.

31. The compound of claim 30 wherein the conjugation group is an active ester.

32. The compound of claim 18, 21, 24 or 26 wherein the targeting molecule is a monoclonal antibody or an antigen binding fragment thereof.

33. A method for radiolabeling a targeting molecule, comprising reacting a compound of claim 1, 4, 7, or 10, wherein P' represents a conjugation group, with a targeting molecule, thereby attaching the compound to said targeting molecule, and then radiolabeling the compound.

34. The method of claim 33 wherein said targeting molecule is a monoclonal antibody or an antigen binding fragment thereof.

35. A method for radiolabeling a targeting molecule, comprising reacting a compound of claim 18, 21, 24, or 26, wherein P' represents a conjugation group, with a targeting molecule, thereby attaching said compound to said targeting molecule.

36. The method of claim 35, wherein said targeting molecule is a monoclonal antibody or an antigen binding fragment thereof.

* * * * *